(12) United States Patent
Soo et al.

(10) Patent No.: US 9,301,976 B2
(45) Date of Patent: *Apr. 5, 2016

(54) COMPOSITIONS COMPRISING PERIVASCULAR STEM CELLS AND NELL-1 PROTEIN

(75) Inventors: B. Chia Soo, Beverly Hills, CA (US); Kang Ting, Beverly Hills, CA (US); Bruno M. Peault, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 24 days.

This patent is subject to a terminal disclaimer.

(21) Appl. No.: 13/816,488

(22) PCT Filed: Aug. 19, 2011

(86) PCT No.: PCT/US2011/048393
§ 371 (c)(1),
(2), (4) Date: Aug. 8, 2013

(87) PCT Pub. No.: WO2012/024573
PCT Pub. Date: Feb. 23, 2012

(65) Prior Publication Data
US 2013/0309207 A1 Nov. 21, 2013

Related U.S. Application Data

(60) Provisional application No. 61/401,905, filed on Aug. 19, 2010.

(51) Int. Cl.
*A01N 63/00* (2006.01)
*A61K 35/12* (2015.01)
*A61K 38/17* (2006.01)
*C12N 5/0775* (2010.01)

(52) U.S. Cl.
CPC .............. *A61K 35/12* (2013.01); *A61K 38/1709* (2013.01); *C12N 5/0667* (2013.01); *C12N 5/0668* (2013.01); *C12N 2501/998* (2013.01)

(58) Field of Classification Search
None
See application file for complete search history.

(56) References Cited

U.S. PATENT DOCUMENTS

2007/0264239 A1* 11/2007 Huard et al. ................. 424/93.7

FOREIGN PATENT DOCUMENTS

| WO | WO 2006/089023 A2 | 8/2006 |
| WO | WO 2008/020815 A1 | 2/2008 |
| WO | WO 2008/148105 A1 | 12/2008 |
| WO | WO 2008/155659 A2 | 12/2008 |
| WO | WO 2010/042654 A2 | 4/2010 |

OTHER PUBLICATIONS

Farrington-Rock et al., Circulation, 2004, vol. 100, p, 2226-2232.*
International Search Report of PCT/US2011/048393, 4 pages.
Crisan et al., 2008, "A perivascular origin for mesenchymal stem cells in multiple human organs," *Cell Stem Cell*, 3:301-313.
Sorrentino et al., 2008, "Isolation and characterization of CD146+ multipotent mesenchymal stromal cells," *Experimental Hematology*, 36:1035-1046.
Varma et al., 2007, "Phenotypical and functional characterization of freshly isolated adipose tissue—derived stem cells," *Stem Cells and Development*, 16: 91-104.
Baksh et al., 2007, "Comparison of proliferative and multi lineage differentiation potential of human mesenchymal stem cells derived from umbilical cord and bone marrow," *Stem Cells*, 25:1384-1392.
Extended European Search Report for EP App. No. 11 818 825.9, 7 pages.
Zimmerlin L. et al., 2009, "Stromal vascular progenitors in adult human adipose tissue," *Cytometry Part A*, 9999A: 22-30.
Crisan M. et al., 2009, "Perivascular Multipotent Progenitor Cells in Human Organs," *Annals of the New York Academy of Sciences*, 1176(1): 118-123.
He W. et al., 2010, "Pericyte-based human tissue engineered vascular grafts," Biomaterials, 31(32): 8235-8244.
Chen C W et al., 2009, "Perivascular multi-lineage progenitor cells in human organs: Regenerative units, cytokine sources or both?," *Cytokine and Growth Factor Reviews*, 20(5-6):429-434.

* cited by examiner

*Primary Examiner* — Kade Ariani
(74) *Attorney, Agent, or Firm* — Duane Morris LLP

(57) ABSTRACT

Embodiments of the present invention provide a population of purified perivascular stem cells (PSC) or induced pluripotent stem cells (iPS) and a supernatant of stem cell free from the stem cell, a composition comprising any of these, and a method of using and making them.

5 Claims, 10 Drawing Sheets

COMPOSITIONS COMPRISING PERIVASCULAR STEM CELLS AND NELL-1 PROTEIN

TECHNICAL FIELD OF THE INVENTION

The present invention generally relates to compositions comprising perivascular stem cells or induced pluripotent stem cells and methods of making and using the same.

BACKGROUND OF THE INVENTION

Regenerative medicine is the process of creating living, functional tissues to repair or replace tissue or organ function lost due to damage, or congenital defects. This field holds the promise of regenerating damaged tissues and organs in the body by stimulating previously irreparable organs to heal themselves. Regenerative medicine also empowers scientists to grow tissues and organs in the laboratory and safely implant them when the body cannot heal itself. Importantly, regenerative medicine has the potential to solve the problem of the shortage of organs available for donation compared to the number of patients that require life-saving organ transplantation, as well as solve the problem of organ transplant rejection, since the organ's cells will match that of the patient (Mason C, Dunnill P (January 2008). "A brief definition of regenerative medicine". *Regenerative Medicine* 3 (1): 1-5). The basis of regenerative medicine is the ability of stem cells to grow into various tissues or organs. Embryonic stem (ES) cells are pluripotent cells capable of both proliferation in cell culture and differentiation towards a variety of lineage-restricted cell populations that exhibit multipotent properties (Odorico et al., Stem Cells 19:193-204 (2001)). Because of these characteristics, ES cells, including human ES cells, can become very specific cell types that perform a variety of functions.

While hESC hold great promise for regenerative medicine, obstacles such as prolonged exposure to animal products in culture medium, teratoma formation, and potential need for immunosuppression remain significant safety issues to clinical hESC use.

The embodiments below address the above problems and needs.

SUMMARY OF THE INVENTION

In one aspect of the present invention, it is provided a population of purified perivascular stem cells (PSC) or induced pluripotent stem cells (iPS), which PSC or iPS being identified by CD146, CD45, CD34, and optional CD31 antibodies as CD146+CD34–CD45– (pericytes) or CD146–CD34+CD45– (adventitial cells). A subset of the PSC or iPS is identified by CD146, CD45, CD34, and CD31 antibodies as CD146+CD34–CD45–CD31– (microvascular pericytes) or CD146–CD34+CD45–CD31– (adventitial cells).

In another aspect of the present invention, it is provided a composition comprising a supernatant of stem cell comprising trophic factors that stimulate the formation of a desired cell or recruitment of a desired progenitor cell so as to form a tissue or organ, and the supernatant comprises a culture medium of stem cell and is free from the stem cell. In some embodiments of the composition, the stem cell is PSC or iPS identified by CD146, CD45, CD34, and optional CD31 antibodies as CD146+CD34–CD45– (pericytes) or CD146–CD34+CD45– (adventitial cells). A subset of the PSC or iPS is identified by CD146, CD45, CD34, and CD31 antibodies as CD146+CD34–CD45–CD31– (microvascular pericytes) or CD146–CD34+CD45–CD31– (adventitial cells). The supernatant can be a liquid, or semi-solid, or solid formulation. In some embodiments, the supernatant is a powder. In some embodiments, the composition further comprises a pharmaceutically acceptable carrier.

In a further aspect of the present invention, it is provided a composition, which composition comprising a population of purified PSC or iPS and optionally an inductive agent, the PSC or iPS are identified by CD146, CD45, CD34, and optional CD31 antibodies as CD146+CD34–CD45– (pericytes) or CD146–CD34+CD45– (adventitial cells), and the inductive agent promotes the differentiation of the PSC or iPS into a desired cell or progenitor cell so as to form a tissue or organ. A subset of the PSC or iPS is identified by CD146, CD45, CD34, and CD31 antibodies as CD146+CD34–CD45–CD31– (microvascular pericytes) or CD146–CD34+CD45–CD31– (adventitial cells). In some embodiments, the composition further comprises an excipient or a pharmaceutically acceptable carrier. The composition can be formulated into any desirable formulation. In some embodiments, the composition is formulated into a scaffold, a bone graft, a cartilage graft, an implant, or a coating on an implantable device. An example of the implantable device is a stent or a suture, which can be resorbable or nonresorbable. In some embodiments, the inductive agent is a Nell-1 peptide.

In a further aspect of the present invention, it is provided a method of treating or ameliorating a medical condition. The method comprises administering to a subject:

a population of purified perivascular stem cells (PSC) or iPS, a composition comprising a population of purified perivascular stem cells (PSC) or iPS, or a composition comprising a supernatant of stem cell free from the stem cell, wherein the medical condition is associated with an injured or diseased tissue or organ or tissue or organ otherwise damaged by a disease or pathogen.

In some embodiments of the method, the medical condition is associated with an injured or diseased tissue or organ. For example, the medical condition can be a CNS (central nervous system) disease, a PNS (peripheral nervous system) disease, skin scarring, fibrosis, a tumor, cartilage injury, defect, or disease, a bone injury, defect, or disease, a cardiac condition, a kidney condition, a sport injury, a respiratory track disease, or diabetes. In some embodiments, the medical condition is one of Alzheimer's disease, Parkinson's disease, liver fibrosis, breast cancer, osteoporosis, heart attack, heart ischemia, renal ischemia, stroke, brain ischemia, injury to the spinal cord, meniscus tear, asthma, a lung disease, or type I diabetes. Other examples of diseases include all conditions listed in the International Classification of Diseases (ICD) and Current Procedural Terminology (CPT) editions.

In some embodiments of the method, the composition is according to any of the embodiments of invention disclosed above or below.

In some embodiments of the method, the tissue or organ is any of the tissue or organ described in the embodiments of composition of invention.

In further aspect of the present invention, it is provided a method of fabricating a composition. The method comprises:

providing a population of purified perivascular stem cells (PSC) or iPS or a supernatant of stem cell free from the stem cell, and forming a composition comprising the population of purified perivascular stem cells (PSC) or iPS or the supernatant of stem cell.

In some embodiments of the method, the composition is according to any of the embodiments of invention disclosed above or below.

DETAILED DESCRIPTION OF THE INVENTION

Figure 1:
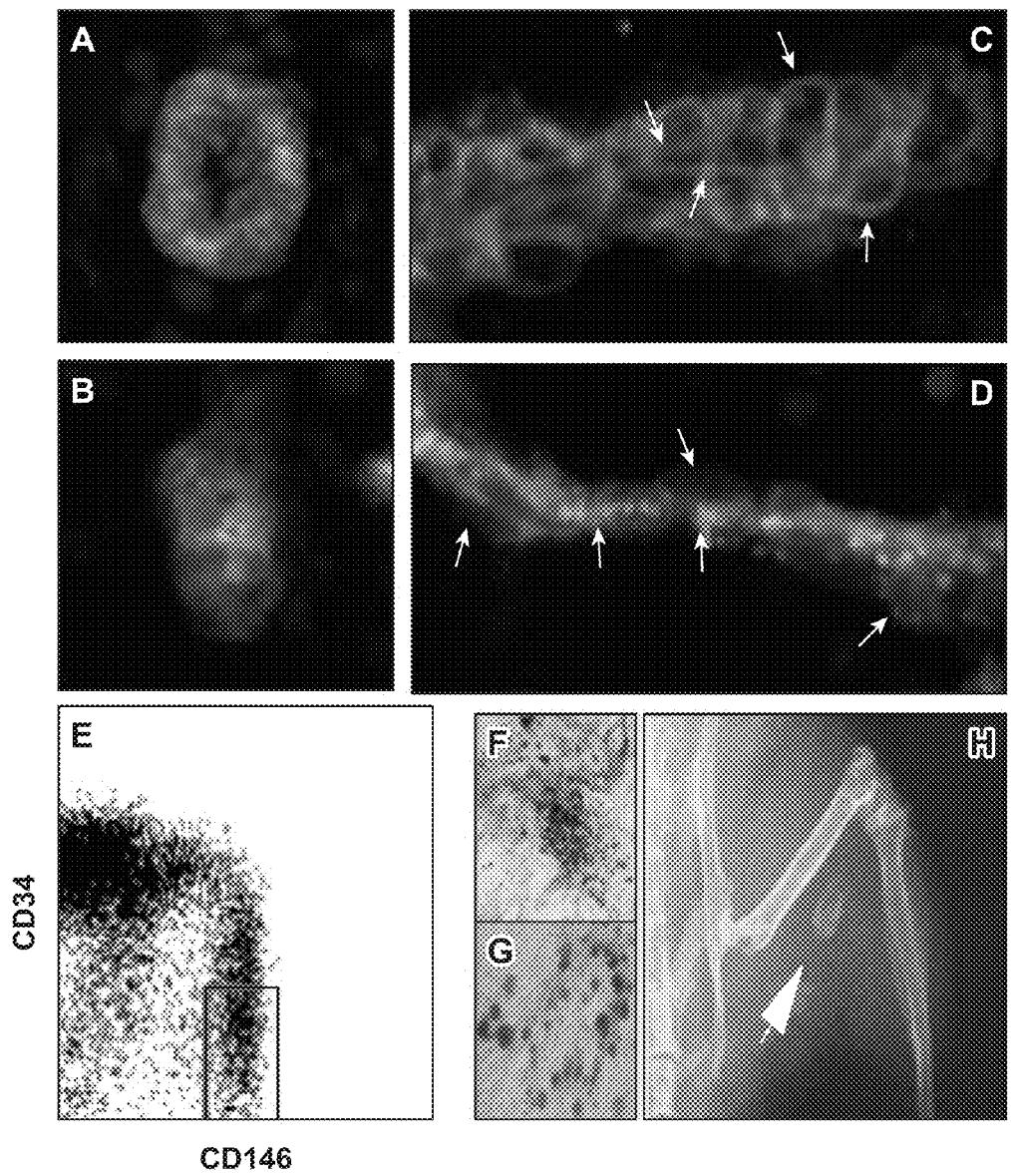
FIGS. 1A-1H show pericytic MSC. All human pericytes express CD146 (A, green; endothelial CD34 is red; B, red; CD34 is green), NG2 (C, green; endothelial VE-cadherin is red) and PDGF-Rβ (D, red; endothelial von Willebrand factor (vWF) is green). E: Pericytes are purified by fluorescence activated cell sorting (FACS) as CD45−CD56−CD146+ CD34− cells (red gate). Pericytes cultivated in osteogenic medium for 21 days: F, von Kossa staining; mineral deposits appear in black. G, alizarin red staining; calcium deposits are stained red. H: Pericytes embedded in a Gelfoam sponge in the presence of BMP2 were implanted in a SCID-NOD mouse muscle pocket. X-ray analysis at day 30 after implantation.

In one aspect of the present invention, it is provided a population of purified perivascular stem cells (PSC) or induced pluripotent stem cells (iPS), which PSC or iPS are identified by CD146, CD45, CD34, and optional CD31 antibodies as CD146+CD34−CD45− (pericytes) or CD146− CD34+CD45− (adventitial cells). A subset of the PSC or iPS is identified by CD146, CD45, CD34, and CD31 antibodies as CD146+CD34−CD45−CD31− (microvascular pericytes) or CD146−CD34+CD45−CD31− (adventitial cells).

In another aspect of the present invention, it is provided a supernatant of stem cell. The supernatant comprises trophic factors that stimulate the formation of a tissue or organ. The supernatant comprises a culture medium of stem cell and is free from the stem cell. In some embodiments, the stem cell is PSC such as pericyte or adventitial cell. The supernatant can be used as liquid or dried so as to be used as powder. In some embodiments, the supernatant can include a carrier or excipient.

In another aspect of the present invention, it is provided a composition, which composition comprising a population of purified PSC or iPS. In some embodiments, the composition can optionally include an inductive agent. The composition can further include an excipient or carrier. In some embodiments, the carrier is a pharmaceutically acceptable carrier. In some embodiments, the composition can be formulated into a scaffold, a bone graft, a cartilage graft, an implant, or a coating on an implantable device, e.g., a coating coated on the luminal surface and/or a luminal surface of a stent.

In a further aspect of the present invention, it is provided a method of treating or ameliorating a medical condition. The method comprises administering to a subject a population of purified perivascular stem cells (PSC) or iPS, a supernatant of stem cell, or a composition disclosed herein. The medical condition is associated with an injured or diseased tissue or organ or tissue or organ otherwise damaged by a disease or pathogen. In some embodiments, the medical condition is any of injured or diseased tissue or organ.

In some embodiments, the PSC or iPS can be induced to differentiate into, and the supernatant can promote the formation of, fibroblast or progenitor cells so as to treat, prevent, or ameliorate a scarring condition, e.g., fibrosis, of a subject, e.g., a mammal. Alternatively, the PSC or iPS can excrete, and the supernatant includes chemical substances so as to treat, prevent, or ameliorate a scarring condition, e.g., fibrosis, of a subject, e.g., a mammal.

In some embodiments, the PSC or iPS can be induced to differentiate into, and the supernatant can promote formation of, myocytes, adipose cells, tenocytes, or connective tissue cells or progenitor cells so as to treat, prevent, or ameliorate a condition pertaining to muscle, fat, tendon, connective tissue, etc. in a mammal. Specific applications of such compositions in this aspect include, for example, breast(s) tissue regeneration, tendon or connective tissue regeneration, etc.

In some embodiments, the PSC or iPS can excrete, and the supernatant comprises, anti-tumor chemical substances or factors so as to treat, prevent, or ameliorate a tumor condition (e.g., a cancer) in a mammal.

In some embodiments, the PSC or iPS can be induced to differentiate into, and the supernatant can promote the formation of, blood cells or progenitor cells so as to treat, prevent, or ameliorate a blood condition in a mammal.

In some embodiments, the PSC or iPS and the supernatant can be used along with a chondroinductive agent. The chondroinductive agent is in a therapeutically effective amount for causing PSC or iPS to differentiate in the chondrocyte or progenitor cell lineages so as to generate cartilages. Alternatively, the chondroinductive agent can be a chemical or biological agent in a therapeutically effective amount for enhancing the survivability or engraftment of the PSC or iPS where PSC or iPS provide trophic factors to stimulate cartilage generation so as to treat, delay, or ameliorate a cartilage condition.

The PSC can be human PSC or animal PSC, and can be autologous PSC, allograft PSC, or xenograft PSC. The iPS can be human iPS or animal iPS, and can be autologous iPS, allograft iPS, or xenograft iPS. The PSC or iPS can have a density from about $1\times10^4$ to about $1\times10^8$/mL (per 1 mL volume of the composition). In some embodiments, the seeding density can be from about $1\times10^4$ to about $1\times10^6$, from about $1\times10^4$ to about $1\times10^5$, from about $1\times10^5$ to about $1\times10^7$, from about $1\times10^5$ to about $1\times10^6$, from about $1\times10^6$ to about $1\times10^7$/ml, or from about $1\times10^7$ to about $1\times10^8$/ml. Examples of seeding densities can be, e.g., $0.5\times10^4$, $1\times10^4$, $0.5\times10^5$, $1\times10^5$, $0.5\times10^6$, $1\times10^6$, $0.5\times10^7$, $1\times10^7$, or $1\times10^8$/ml.

In some embodiments, the term PSC can be pericytes or adventitia cells.

The composition can be formulated into different formulations. In some embodiments, the composition can be a scaffold. The scaffold can include one or more excipients. In some embodiments, the scaffold can include a plurality of pores, which can load the PSC or iPS. In some embodiments, an agent such as NELL-1 protein can be embedded in the body of scaffold, and the PSC or iPS is seeded in the pores in the scaffold. In some embodiments, the composition can be biodegradable or biodurable.

In another aspect of the present invention, it is provided an implantable device. The implantable device comprises a composition of the various embodiments above.

As used herein the term "tissue" and "organ" are as described below:

In any of the above compositions, the tissues to be formed from the stem cells can be epithelial, connective, muscle, or nervous tissues that typically develop from three primary germ layers: mesoderm, ectoderm, and endoderm. Mesoderm—develops into epithelial tissue, connective tissue and muscle tissue. Ectoderm—develops into nervous tissue and epithelial tissue. Endoderm—develops into epithelial tissue.

Epithelial tissues are made of cells arranged in a continuous sheet with one or more layers, has apical & basal surfaces. A basement membrane is the attachment between the basal surface of the cell & the underlying connective tissue. Two types of epithelial tissues: (1) Covering & lining epithelia and (2) Glandular Epithelium. The number of cell layers & the shape of the cells in the top layer can classify epithelium: (1) Simple Epithelium—one cell layer, (2) Stratified epithelium—two or more cell layers, (3) Pseudostratified Columnar Epithelium—When cells of an epithelial tissue are all anchored to the basement Membrane but not all cells reach the apical surface and (4) Glandular Epithelium—(i) Endocrine: Release hormones directly into the blood stream and (ii) Exocrine—Secrete into ducts.

Connective tissues contain many different cell types including: fibroblasts, macrophages, mast cells, and adipocytes. Connective Tissue Matrix is made of two materials: ground substance—proteins and polysaccharides, fiber—reticular, collagen and elastic. Connective Tissues can be further classified as: (1) Loose Connective—fibers & many cell types in gelatinous matrix, found in skin, & surrounding blood vessels, nerves, and organs; (2) Dense Connective—Bundles of parallel collagen fibers& fibroblasts, found in tendons& ligaments; and (3) Cartilage—Cartilage is made of collagen & elastin fibers embedded in a matrix glycoprotein & cells called chondrocytes, which was found in small spaces. Furthermore, cartilage has three subtypes: (1) Hyaline cartilage—Weakest, most abundant type, Found at end of long bones, & structures like the ear and nose; (2) Elastic cartilage—maintains shape, branching elastic fibers distinguish it from hyaline; and (3) Fibrous Cartilage—Strongest type, has dense collagen & little matrix, found in pelvis, skull & vertebral discs.

Muscle tissues are divided into 3 categories: (1) Skeletal Muscle—voluntary, striated, striations perpendicular to the muscle fibers and it is mainly found attached to bones; (2) Cardiac Muscle—involuntary, striated, branched and has intercalated discs; and (3) Smooth Muscle—involuntary, nonstriated, spindle shaped and is found in blood vessels & the GI tract.

Nervous tissues consist of two cell types in the central nervous system (CNS) & peripheral nervous system (PNS): (1) Neurons—Cells that convert stimuli into electrical impulses to the brain and (2) Neuroglia—supportive cells. Neurons are made up of cell body, axon and dendrites with three subtypes: (1) Motor Neuron—carry impulses from CNS to muscles and glands, (2) Interneuron—interpret input from sensory neurons and end responses to motor neurons, and (3) Sensory Neuron—receive information from environment and transmit to CNS. Meanwhile, Neuroglia are made up of astrocytes, oligodendrocytes, ependymal cells and microglia in the CNS, and schwann cells and satellite cells in the PNS.

After the 4 primary tissue types, organs are the next level of organization in the body. An organ is a structure that contains at least two different types of tissue functioning together for a common purpose. An organ system is comprised of two or more different organs that work together to provide a common function. The 10 major organ systems in the body are: skeletal (e.g., bones, cartilage, tendons, and ligaments), muscular (e.g., skeletal and smooth muscles), circulatory (e.g., heart, blood vessels, and blood), nervous (e.g., brain, spinal cord, and peripheral nerves), respiratory (e.g., nose, trachea, and lungs), digestive (e.g., mouth, esophagus, stomach, small and large intestines), excretory (e.g., kidneys, ureters, bladder, and urethra), endocrine (e.g., hypothalamus, pituitary, thyroid, pancreas, and adrenal glands), reproductive (e.g., ovaries, oviducts, uterus, vagina, mammary glands, testes, seminal vesicles, and penis), and lymphatic/immune (e.g., lymph nodes and vessels, lymph, while blood cells, T- and B-cells). Other tissues/organs/complex structures include but are not limited to skin, liver, stroma, meniscus, periodontal tissue, retina, cornea, eye, a facial organ, a limb, or other body part.

As used herein, the term tissue or organ shall mean any tissue or organ in a mammalian subject. Such tissue or organ can be, e.g., any of facial organs (e.g., nose, facial skin, lips, retina, or ear), a limb, arteries, veins, adipose, or any interior organ such as an oral tissue or organ (dental tissue, periodontal tissue, tongue, teeth), brain, cardiac organ or tissue (e.g., heart, heart valves, arteries, and veins), a pulmonary tissue or organ (e.g., lung or trachea, or bronchus), a gastrointestinal tissue or organ, breasts, pancreas, liver, urinary tract, spinal cord, bone marrow, kidney, meniscus, bladder or skin. In some other embodiments, the tissue can be, bone, cartilage, muscle, marrow, tendon or ligament, or a connective tissue.

As used herein, the term "trophic factor" refers to any nutrients or factors excreted by a stem cell. Such trophic factors can be, e.g., immuno-modulatory factors, such as TNF-α, IL-12, IL-10, IL-4, IgG CXCR4, IgM CXCR5, IgA CR7, IFN-γ, HGF, TGF-β1, factors that prevent or reduce scar formation, factors that promotes antiogenesis, cytoprotective or anti-apoptotic factors, mitotic factors, factors that promote tissue regeneration or cell matrix materials such as hyaluronic acid.

As used herein, the term "therapeutically effective amount" means the dose of chondroinductive agent (e.g., a NELL-1 factor) required for causing a PSC to differentiate into a chondrocyte or progenitor cell to achieve cartilage regeneration or for enhancing the survivability or engraftment of the PSC or iPS where PSC or iPS provide trophic factors to stimulate cartilage generation so as to treat, delay, or ameliorate a cartilage condition.

As used herein, the term "inductive agent" refers to a local or systemic substances or conditions that promote the differentiation into or formation of a desired cell or tissue. Examples of such substances can be systemic or local products of a cell or a tissue, small molecules, biomimetic or dynamic scaffolds (e.g., application of mechanical force, http://www.ibridgenetwork.org/ucm/dynamic-scaffolds-to-promote-cell-differentiation), or conditions that promote growth/differentiation (e.g., oral vitamin D or L-glutamine supplementation, http://www.springerlink.com/content/a34m95177w5vn8t1/), or combinations thereof (e.g., http://www.ncbi.nlm.nih.gov/pubmed/19831634) which are well documented in the art. For example, angiogenesis inductive agent includes growth factors (ECGF1, FGF1, FGF13, FGF2, FGFBP1, FIGF, GRN, GRP, HGF, KITLG, LEP, MDK, PDGFB, PDGFD, PGF, PROK1, TGFA, VEGFA), cytokines and chemokines_(BMP2, CCL15, CCL2, CSF3, CXCL11, CXCL12, CXCL13, CXCL14, CXCL3, CXCL5, CXCL6, CXCL9, IL10, IL6, IL8, PPBP, PTN, TNF) (see, e.g., http://www.sabiosciences.com/rt_per_product/HTML/PAHS-024A.html), and other positive regulators of angiogenesis (AGGF1, AMOT, ANG, ANGPT1, BTG1, EDIL3, EREG, FST, RHOB, RUNX1). Alternatively, angiogenesis inhibiting agents include cytokines, chemokines and growth factors (CXCL10, CXCL2, IFNG, IL12A, IL12B, IL17F, PF4, TGFB1) and other negative regulators of angiogenesis (ANGPT2, ANGPTL1, BAIL CD55, CD59, CHGA, COL18A1, COL4A3, FN1, IFNA1, IFNB1, KLK3, MLLT7, NPPB, NPR1, PLG, PRL, RNH1, SERPINC1, SERPINE1, SERPINF1, SPINK5, STAB1, THBS1, TIE1, TIMP1, TIMP2, TIMP3, TNNI2, TNNI3).

Examples of chondrogenesis inductive agents include TGF-13 superfamily of secreted proteins such as transforming growth factor-beta (TGF-beta), and bone morphogenetic proteins (BMPs) (e.g., GDF5, GDF6, GDF7, BMP2, BMP4, and BMP7,), parathyroid hormone-related protein, Hedgehog family proteins, mammalian family of lipid-modified Wnt glycoproteins, fibroblast growth factor family, and vascular endothelial growth factor (VEGF) (see, e.g., Kronenberg et al., CSH Monographs, Volume 53 (2009): The Skeletal System). Examples of osteoinductive agents include BMPs, TGF-beta, fibroblast growth factor (FGF), insulin-like growth factor (IGF), VEGF, angiopoietins, platelet-derived growth factor (PDGF), epidermal growth factor, parathyroid hormone (related protein) (PTH/PTHrP), and interleukins (IL), and platelet-rich plasma (PRP) isolates (see, e.g., Kempen, et al., Tissue Engineering: Part B, 2010, 16(6):551-566; Nauth, et al., J Orthop Trauma, 2010;24:543-546).

As used herein, the term "chondroinductive agent" refers to a chemical or biological agent which is effective for promoting cartilage formation or for enhancing the survivability or engraftment of the PSC or iPS where PSC or iPS provide trophic factors to stimulate cartilage generation so as to treat, delay, or ameliorate a cartilage condition. An example of the chondroinductive agent is a NELL-1 protein. As used herein, the term biological agent refers to anything pertaining to DNA or amino acid and can be, for example, cell, cell factor, gene therapy, plasmid, or proteins or peptides, etc.

As used herein, the terms "NELL-1 protein", "NELL-1 peptide" and "NELL-1 factor" are sometimes used interchangeably.

As used herein, the terms "medical condition", "disease" and "disorder" are used interchangeably.

As used herein, the terms "sport injury" and "sports injury" are used interchangeably and refer to an injury to or condition of a soft or skeletal tissue or organ, e.g., a nervous tissue, muscular tissue, bone, or cartilage injury. In some embodiments, such injuries or conditions can be an injury to or condition of muscle, tendon, rotator cuff, or any concerns of sports medicine such as these described in http://www.childrensmemorial.org/depts/sportsmedicine/healthtopics.aspx and http://www.reportsnreports.com/reports/25322-us-market-for-orthopedic-soft-tissue-and-sports-medicine-2010.html.

Cell-Based Therapies

Cell-based therapies are well documented to be effective for treating or ameliorating a disorder by regeneration of a cell (see, e.g., Arnold I. Caplan, Treatment of Human Diseases: Cell-based Therapies using Adult Mesenchymal Stem Cells", NJ Symp Biomat & Regen. Med., Oct. 8, 2008). The PSC, iPS, or supernatant of the various embodiments disclosed above can be used to treat or ameliorate any of these disorders.

Medical conditions that can be treated or ameliorated by the PSC, iPS, compositions, or supernatant of the various embodiments disclosed herein can be any condition pertaining to an injured or diseased organ or tissue. Such organs or tissues are described above.

In some embodiments, the medical condition is a disease in the central nerve system (CNS). Such CNS diseases can relate to the spinal cord or the brain and can be caused by trauma, infection, degeneration, structural defects, tumor, or autoimmune disorders. Examples of such CNS diseases include, Alzheimer's disease, Parkinson's disease, encephalitis, meningitis, tropical spastic paraparesis, arachnoid cysts, Huntington's disease, locked-in-syndrome, Tourette's disease, and multiple sclerosis.

In some embodiments, the medical condition pertains to scar formation in a tissue. Such medical conditions can be, e.g., skin scarring, or fibrosis.

In some embodiments, the medical condition pertains to muscle, fat, tendon, connective tissue, etc. in a mammal. Specific applications of such compositions in this aspect include, for example, breast(s) tissue regeneration, tendon or connective tissue regeneration, etc.

In some embodiments, the medical condition pertains to a tumor condition (e.g., a cancer) in a mammal.

In some embodiments, the medical condition pertains to a blood condition (e.g., leukemia) in a mammal.

In some embodiments, the medical condition pertains to cartilage injury, defect or disease.

In some embodiments, the medical condition can be a bone related condition, e.g., injury to bone. In some embodiments, the bone related condition can be any one that pertains to bone regeneration, musculoskeletal injuries, bone repair, or osteoporosis. Bone repair can be achieved by providing to a subject needing treatment osteogentic stem cells, osteoconductive surfaces, and/or osteoinductive growth factors. For example, embodiments of the prevent invention described above or below can be used (1) for lumbar spin fusion as, e.g., autologous bone graft substitute for single application lumbar spine fusion or (2) for tibial fracture repair to treat acute, open tibial shaft fractures that have been stabilized with intramedullar nail fixation.

In some embodiments, the medical condition can be a cardiac condition. Such cardiac condition can be, e.g., cardiac ischemia.

In some embodiments, the medical condition can be a kidney condition. Such kidney condition can be, e.g., renal ischemia.

In some embodiments, the medical condition can be a brain condition. Such brain condition can be, e.g., stroke or brain ischemia.

In some embodiments, the medical condition can be a spine condition. Such spine condition can be, e.g., injury to the spinal cord.

In some embodiments, the medical condition can be a sport injury condition. Such sport injury condition can be, e.g., meniscus tear.

Other exemplary medical conditions include, e.g., asthma or other respiratory track diseases, type I diabetes, and conditions listed in the International Classification of Diseases (ICD) and Current Procedural Terminology (CPT) editions.

In some embodiments, the cell-based therapy is cartilage regeneration. Cartilage regeneration can be achieved using mesenchymal stem cells (MSC) technology. Various methods of cartilage regeneration using mesenchymal stem cells are reported (see, e.g., Uematsu, K., Biomaterials. 26(20):4273-9 (2005)) and reviewed in Chen, et al., NATURE CLINICAL PRACTICE RHEUMATOLOGY 2(7):373-382 (2006); Galle, J., et al., Current Medicinal Chemistry, Volume 17, Number 21, July 2010, pp. 2274-2291(18)). PSC is reportedly a perivascular ancestor of MSCs (see, e.g., Crisan, et al., Cell Stem Cell 3:301-33 (2008); Corselli, et al., Arterioscler Thromb Vasc Biol 30:1104-1109 (2010)).

Advantages of using PSC rather than MSCs for cartilage regeneration are multi-facets. The majority of cell expansion or culturing procedures are based on the use of fetal bovine serum (FBS), which carries the risk of xenoimmunization [e.g., nonhuman immunogenic sialic acid (Neu5Gc)] and transmission of known (e.g., prions transmitting bovine spongiform encephalopathy) and unknown pathogens. Also, irrespective of culture medium, ex vivo culture increases the risk of microbiological or particulate contamination as well as genetic instability (Dahl, J. A. et al. Genetic and epigenetic instability of human bone marrow mesenchymal stem cells expanded in autologous serum or fetal bovine serum. Int J Dev Biol 52, 1033-42 (2008)). From a safety standpoint, the use of freshly harvested and sorted PSC is superior to cultured MSC such as ASC because it decreases immunogenic, infectious, and tumorigenic risks.

Other advantages of PSC use over MSC are: 1] precise characterization in terms of native tissue localization, phenotype and developmental potential, (MSC are retrospectively derived from primary, heterogeneous cell cultures) and 2] improved trophic potency (we have determined that PSC secrete 10-20 times more heparin binding epidermal growth factor and 3-7 times more basic fibroblast growth factor and vascular endothelial growth factor than classically derived adipose tissue and cord blood MSC (Chen, C. W. et al. Cytokines and Growth Factors Reviews, 20(5):429-434 (2009)). Thus from an FDA regulatory perspective using PSC will facilitate demonstration of product identity, purity, sterility, safety, and potency.

In some embodiments, the cell-base therapy provides a therapy for sports injury or condition. Such injury or condition can be an injury to or condition of a soft or skeletal tissue or organ, e.g., a nervous tissue, muscular tissue, bone, or cartilage injury. In some embodiments, such injuries or conditions can be an injury to or condition of muscle, tendon, rotator cuff, or any concerns of sports medicine such as these described in http://www.childrensmemorial.org/depts/sportsmedicine/healthtopics.aspx and http://www.reportsnreports.com/reports/25322-us-market-for-orthopedic-soft-tissue-and-sports-medicine-2010.html. In some embodiments, such cell-based therapy is Anterior/Posterior Cruciate Ligament (ACL/PCL) Reconstruction, ACL/PCL fixation, cartilage repair, meniscal cartilage repair, rotator cuff repair, shoulder labrum repair, rotator cuff graft reinforcement, or nerve conduit repair or regeneration.

PSC and iPS

As used herein, the term perivascular stem cells (PSC) shall encompass pericyte and adventitia cells Isolation of PSC is well documented. For example, pericyte cells were isolated from various tissues by Peault and Huard in U.S. application Ser. No. 11/746,979. Isolation of adventitial cells from various tissues is well documented (data not shown).

PSC have been isolated from essentially all tissues tested including skeletal muscle, pancreas, placenta, adipose, brain, heart, skin, lung, eye, gut, bone marrow, umbilical cord, or teeth. In some embodiments, autologous PSC can be purified through fluorescence activated cell sorting (FACS) from the stromal vascular fraction of adipose tissues in numbers sufficient to achieve clinical efficacy without ex vivo expansion. The following describes an example of isolating pericyte PSC from human skeletal muscle tissues:

Isolation of pericytes. Briefly, skeletal muscle is separated from fat and macro vasculature then minced into small pieces. The muscle is then incubated (e.g., for 45 min at 37° C.) in medium containing DMEM high glucose (Gibco), 20% FBS (Gibco), 1% Penicillin-Streptomycin (PS) (Gibco) and complemented by 0.5 mg/ml of each collagenases type I, II, and IV. The resulting cell suspension was filtered to eliminate all debris. After rinsing, cells are FACS-sorted according to positive expression for CD 146, NG2 (a proteoglycan associated with pericytes during vascular morphogenesis) and PDGF-R13, and to the absence of hematopoietic (CD45), endothelial (CD34), and myogenic (CD56) cell markers. The dead cells are excluded by FACS via propidium iodure staining. Sorted pericytes are seeded (e.g., at $2\times10^4$ cells/cm$^2$ in endothelial cell growth medium 2 (EGM-2, Cambrex Bioscience)) and cultured (e.g., at 37° C. for 2 weeks in plates coated with 0.2% gelatin (Calbiochem)). Pericytes are trypsinized once a week and cultured (e.g., at 1:3 dilution (from passage 1 to 5) then at 1:10 (after passage 5)). Except for the first passage, all pericytes are cultured (e.g., in DMEM/FBS/PS proliferation medium) in uncoated flasks to maintain their original phenotype. Pericytes between passages 9 and 11 are used for all tests.

Isolation of adventitia PSC is exemplified by the procedure described in Example 1.

Formation of iPS is well documented (see, e.g., Okita, K, et al., Nature 448 (7151): 313-7 (2007); Maherali N, et. al., Cell Stem Cell 1:55-70 (2007); and Wernig, M; et al., Nature 448 (7151): 318-24 (2007). An exemplary step-by-step procedure of forming and sorting iPS is described in detail in Park, et al., Nature Protocols, 2008, 3(7):1180-1186, the teaching of which is incorporated herein in its entirety by reference.

NELL-1 Factor

"A NELL-1 factor" as used herein, includes wild type (i.e., naturally occurring) Nell 1 proteins of any mammalian origin, such as human, murine, rat and the like. Exemplary NELL-1 factors for use in the present invention include human NELL-1 protein (SEQ ID NO: 1), murine NELL-1 protein (SEQ ID NO: 2), and rat NELL-1 protein (SEQ ID NO: 3).

"A NELL-1 factor" as used herein, also includes functional derivatives of a wild type NELL-1 protein. A "functional derivative" refers to a modified NELL-1 protein which has one or more amino acid substitutions, deletions or insertions as compared to a wild type NELL-1 protein, and which retains substantially the activity of a wild type NELL-1 protein. By "substantially" is meant at least 50%, at least 75%, or even at least 85% of the activity of a wild type NELL-1 protein. According to the present invention, in order for the functional derivative to substantially retain the activity or function of a wild type NELL-1 protein, the functional NELL-1 derivative shares a sequence identity with the wild type NELL-1 protein of at least 75%, at least 85%, at least 95% or even 99%.

The structure of NELL-1 proteins has been characterized (see, e.g., Kuroda et al., 1999a; Kuroda et al., 1999b, Desai et al., 2006). For example, the murine NELL-1 protein (SEQ ID NO: 4) is a protein of 810 amino acids, having a secretion signal peptide (amino acids #1 to 16), an N-terminal TSP-like module (amino acids #29 to 213), a Laminin G region (amino acids #86 to 210), von Willebrand factor C domains (amino acids #273 to 331 and 699 to 749), and a $Ca^{1+}$-binding EGF-like domains (amino acids #549 to 586).

The secretion signal peptide domain of NELL-1 protein is an amino acid sequence in the protein that is generally involved in transport of the protein to cell organelles where it is processed for secretion outside the cell. The N-terminal TSP-like module is generally associated with heparin binding. von Willebrand factor C domains are generally involved with oligomerization of NELL-1. Laminin G domains of NELL-1 protein are generally involved in adherence of NELL-1 protein to specific cell types or other extracellular matrix proteins. The interaction of such domains with their counterparts is generally associated with, for example, processes such as differentiation, adhesion, cell signaling or mediating specific cell-cell interactions in order to promote cell proliferation and differentiation. The $Ca^{2+}$-binding EGF-like domains of NELL-1 binds protein kinase C beta, which is typically involved in cell signaling pathways in growth and differentiation.

The amino acid sequence of NELL-1 protein is very highly conserved, especially across mammalian species. For example, the murine NELL-1 protein shares about 93% sequence identity with the human NELL-1 protein (SEQ ID NO: 1), which, in turn, shares about 90% sequence identity with the rat NELL-1 protein (SEQ ID NO: 2). Those skilled in the art can use any of the well-known molecular cloning techniques to generate NELL-1 derivatives having one or more amino acid substitutions, deletions or insertions, taking into consideration the functional domains (e.g., secretion signal peptide sequence, N-terminal TSP-like module, Laminin G region, von Willebrand factor C domain) of NELL-1. See, for example, Current Protocols in Molecular Cloning (Ausubel et al., John Wiley & Sons, New York).

The minimum length of a NELL-1 functional derivative is typically at least about 10 amino acids residues in length, more typically at least about 20 amino acid residues in length, even more typically at least about 30 amino acid residues in length, and still more typically at least about 40 amino acid residues in length. As stated above, wild type NELL-1 protein is approximately about 810 amino acids residues in length. A NELL-1 functional derivative can be at most about 810 amino acid residues in length. For example, a NELL-1 functional derivative can be at most at most about 820, 805, 800, 790, 780, 750, 600, 650 600, 550, etc. amino acid residues in length.

Once a NELL-1 protein derivative is made, such protein can be tested to determine whether such derivative retains substantially the activity or function of a wild type NELL-1 protein. For example, the ability of a NELL-1 derivative to bind PKC beta can be tested. Suitable assays for assessing the binding of NELL-1 to PKC beta is described in e.g., Kuroda et al. (1999b). For example, protein-protein interaction can be analyzed by using the yeast two-hybrid system. Briefly, a modified NELL-1 protein can be fused with GAL4 activating domain and the regulatory domain of PKC can be fused with the GAL4 DNA-binding domain. The activity of beta-galactosidase in yeast cells can be detected.

In addition, one can also test the ability of a NELL-1 derivative to stimulate differentiation of precursor cells, which are in the chondrocyte lineage, towards mature chondrocytes. Maturity of chondrocytes can be assessed cellularly (histology) and molecularly (expression of cardiac-specific proteins or extracellular matrix materials). Still further, as an alternative assay, a NELL-1 derivative can be tested for its ability to drive osteoblast precursors to mature bone cells, by detecting expression of late molecular bone markers or mineralization (i.e., calcium deposits). By comparing the activity of a NELL-1 derivative with that of a wild type NELL-1 protein in one or more of the assays such as those described above, one should be able to determine whether such derivative retains substantially the activity or function of a wild type NELL-1 protein.

A NELL-1 protein or functional derivative thereof may be prepared by methods that are well known in the art. One such method includes isolating or synthesizing DNA encoding the NELL-1 protein, and producing the recombinant protein by expressing the DNA, optionally in a recombinant vector, in a suitable host cell, including bacterial, yeast, insect or mammalian cells. Such suitable methods for synthesizing DNA are, for example, described by Caruthers et al. 1985. Science 230:281-285 and DNA Structure, Part A: Synthesis and Physical Analysis of DNA, Lilley, D. M. J. and Dahlberg, J. E. (Eds.), Methods Enzymol., 211, Academic Press, Inc., New York (1992).

The term "therapeutically effective amount" means the dose required to cause a PSC to differentiate into a cartilage cell or progenitor cell to achieve cartilage regeneration so as to treat, delay, or ameliorate a cartilage condition. Precise dosages depend on the cartilage cell type, disease state or condition being treated and other clinical factors, such as weight and condition of the subject, the subject's response to the therapy, the type of formulations and the route of administration. As a general rule, a suitable dose of a NELL-1 composition (i.e., including a NELL-1 protein or nucleic acid) for the administration to adult humans ranges from about 0.001 mg to about 20 mg per kilogram of body weight. In some embodiments, a suitable dose of a NELL-1 composition for the administration to adult humans is in the range of about 0.01 mg to about 5 mg per kilogram of body weight. However, the precise dosage to be therapeutically effective and non-detrimental can be determined by those skilled in the art.

NELL-1 protein and method of making the protein has been described in U.S. application Ser. Nos. 10/544,553, 11/392,294, 11/713,366, and 11/594,510, and U.S. Pat. No. 7,052,856. The teachings in these applications and patent are incorporated herein by reference.

Formulations and Carriers

The composition disclosed herein can be formulated into different formulations. The composition can include materials and carriers to effect a desired formulation. For example, the composition can include an injectable or moldable material that can set within a pre-defined period of placement. Such a pre-defined period can be, e.g., 10 minutes, 30 minutes, one hour, two hours, etc.

In some embodiments, the composition can include a chemical gel that includes primary bonds formed due to changes in pH, ionic environment, and solvent concentration. Examples of such chemical gels can be, but are not limited to, polysaccharides such as chitosan, chitosan plus ionic salts such as beta-glycerophosphates, aginates plus $Ba^{2+}$, $Sr^{2+}$, $Ca^{2+}$, $Mg^{2+}$, collagen, fibrin, plasma or combinations thereof.

In some embodiments, the composition can include a physical gel that includes secondary bonds formed due to temperature changes. Examples of such physical gels can be, but are not limited to, alginate, poly(ethylene glycol)-poly (lactic acid-co-glycolic acid)-poly(ethylene glycol) (PEG-PLGA-PEG) tri-block copolymers, agarose, and celluloses. In some embodiments, physical gels that can be used in the composition described herein can include physical gels that are liquid under high shear but gels to solid at low shear. Examples of such physical gels include, but are not limited to, hyaluronic acid, or polyethylene oxides. The physical gels can have pre-formed materials with pre-defined dimensions and shape.

In some embodiments, the composition described herein can include a material that degrade or release active agents in response to a stimulus. Some examples of such stimuli are mechanical stimuli, light, temperature changes, pH changes, change of ionic strength, or electromagnetic field. Such materials are known in the art. Some examples of such materials are chitosan, alginates, pluronics, methyl cellulose, hyaluronic acids, and polyethylene oxides. Other examples are described by Brandl F, Sommer F, Goepferich A. "Rational design of hydrogels for tissue engineering: Impact of physical factors on cell behavior" in Biomaterials. Epub 2006 Sep. 29.

In some embodiments, the composition described herein including any of the gels described above can further include a crosslinker to further tailor degradation kinetics and controlled release. Alternatively, in some embodiments, the composition described herein can include an interpenetrating phase composite or interpenetrating network (IPN) that includes any of the above described gels. Some examples of the crosslinker includes, but are not limited to, common crosslinking agents (polyalkylene oxide, ethylene dimethacrylate, N,N'-methylenebisacrylamide, methylenebis(4-phenyl isocyanate), ethylene dimethacrylate, divinylbenzene, allyl methacrylate, carbodiimidazole, sulfonyl chloride, chlorocarbonates, n-hydroxysuccinimide ester, succinimidyl ester, epoxides, aryl halides, sulfasuccinimidyl esters, and maleimides); PEG based crosslinkers (e.g. MAL-dPEGx-NHS-esters, MAL-dPEGx acid, Bis-MAL-dPEGx, etc.) and photo/light activated crosslinkers, N-hydroxysuccinimide-based crosslinkers, dilysine, trilysine, and tetralysine.

The composition described herein can include a carrier. The carrier can be a polymeric carrier or non-polymeric carrier. In some embodiments, the carrier can be biodegradable, such as degradable by enzymatic or hydrolytic mechanisms. Examples of carriers include, but are not limited to synthetic absorbable polymers such as such as but not limited to poly (α-hydroxy acids) such as poly(L-lactide) (PLLA), poly(D, L-lactide) (PDLLA), polyglycolide (PGA), poly(lactide-co-glycolide) (PLGA), poly(-caprolactone), poly(trimethylene carbonate), poly(p-dioxanone), poly(-caprolactone-co-glycolide), poly(glycolide-co-trimethylene carbonate) poly(D, L-lactide-co-trimethylene carbonate), polyarylates, polyhydroxybutyrate (PHB), polyanhydrides, poly(anhydride-co-imide), propylene-co-fumarates, polylactones, polyesters, polycarbonates, polyanionic polymers, polyanhydrides, polyester-amides, poly(amino-acids), homopolypeptides, poly(phosphazenes), poly(glaxanone), polysaccharides, and poly(orthoesters), polyglactin, polyglactic acid, polyaldonic acid, polyacrylic acids, polyalkanoates; copolymers and admixtures thereof, and any derivatives and modifications. See for example, U.S. Pat. No. 4,563,489, and PCT Int. Appl. No. WO/03024316, herein incorporated by reference. Other examples of carriers include cellulosic polymers such as, but not limited to alkylcellulose, hydroxyalkylcellulose, methylcellulose, ethylcellulose, hydroxyethylcellulose, hydroxypropylcellulose, hydroxypropyl-methylcellulose, carboxymethylcellulose, and their cationic salts. Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, herein incorporated by reference.

In one embodiment, the carrier can further be coated by compositions, including bioglass and or apatites derived from sol-gel techniques, or from immersion techniques such as, but not limited to simulated body fluids with calcium and phosphate concentrations ranging from about 1.5 to 7-fold the natural serum concentration and adjusted by various means to solutions with pH range of about 2.8-7.8 at temperature from about 15-65 degrees C. See, for example, U.S. Pat. Nos. 6,426,114 and 6,013,591; and PCT Int. Appl. WO/9117965 herein incorporated by reference.

Other examples of carriers include, collagen (e.g. Collastat, Helistat collagen sponges), hyaluronan, fibrin, chitosan, alginate, and gelatin. See for example, PCT Int. Appls. WO/9505846; WO/02085422, herein incorporated by reference.

In one embodiment, the carrier can include heparin-binding agents; including but not limited to heparin-like polymers e.g. dextran sulfate, chondroitin sulfate, heparin sulfate, fucan, alginate, or their derivatives; and peptide fragments with amino acid modifications to increase heparin affinity. See for example, Journal of Biological Chemistry (2003), 278(44), p. 43229-43235, herein incorporated by reference.

In one embodiment, the composition can be in the form of a liquid, solid or gel. In one embodiment, the substrate can include a carrier that is in the form of a flowable gel. The gel can be selected so as to be injectable, such as via a syringe at the site where cartilage formation is desired. The gel can be a chemical gel which can be a chemical gel formed by primary bonds, and controlled by pH, ionic groups, and/or solvent concentration. The gel can also be a physical gel which can be formed by secondary bonds and controlled by temperature and viscosity. Examples of gels include, but are not limited to, pluronics, gelatin, hyaluronan, collagen, polylactide-polyethylene glycol solutions and conjugates, chitosan, chitosan & b-glycerophosphate (BST-gel), alginates, agarose, hydroxypropyl cellulose, methyl cellulose, polyethylene oxide, polylactides/glycolides in N-methyl-2-pyrrolidone. See for example, Anatomical Record (2001), 263(4), 342-349, herein incorporated by reference.

In one embodiment, the carrier can be photopolymerizable, such as by electromagnetic radiation with wavelength of at least about 250 nm. Example of photopolymerizable polymers include polyethylene (PEG) acrylate derivatives, PEG methacrylate derivatives, propylene fumarate-co-ethylene glycol, polyvinyl alcohol derivatives, PEG-co-poly(-hydroxy acid) diacrylate macromers, and modified polysaccharides such as hyaluronic acid derivatives and dextran methacrylate. See for example, U.S. Pat. No. 5,410,016, herein incorporated by reference.

In one embodiment, the composition can include a carrier that is temperature sensitive. Examples include carriers made from N-isopropylacrylamide (NiPAM), or modified NiPAM with lowered lower critical solution temperature (LCST) and enhanced peptide (e.g. NELL-1) binding by incorporation of ethyl methacrylate and N-acryloxysuccinimide; or alkyl methacrylates such as butylmethacrylate, hexylmethacrylate and dodecylmethacrylate (see, e.g., WO/2001070288; U.S. Pat. No. 5,124,151, both herein incorporated by reference).

In one embodiment, where the carrier can have a surface that is decorated and/or immobilized with cell adhesion molecules, adhesion peptides, and adhesion peptide analogs which can promote cell-matrix attachment via receptor mediated mechanisms, and/or molecular moieties which can promote adhesion via non-receptor mediated mechanisms binding such as, but not limited to polycationic polyamino-acid-peptides (e.g. polylysine, polyanionic polyamino-acid-peptides, Mefp-class adhesive molecules and other DOPA-rich peptides (e.g., poly-lysine-DOPA), polysaccharides, and proteoglycans. See for example, WO/2004005421; WO/2003008376; WO/9734016, herein incorporated by reference.

In one embodiment, the carrier can include various naturally occurring matrices or their components such as devitalized cartilage matrix, demineralized bone matrix, or other components derived from allograft, xenograft, or any other naturally occurring material derived from Monera, Protista, Fungi, Plantae, or Animalia kingdoms.

In one embodiment, the carrier can include one or more sequestering agents such as, but not limited to, collagen, gelatin, hyaluronic acid, alginate, poly(ethylene glycol), alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, blood, fibrin, polyoxyethylene oxide, calcium sulfate hemihydrate, apatites, carboxyvinyl polymer, and poly(vinyl alcohol). See for example, U.S. Pat. No. 6,620,406, herein incorporated by reference.

In one embodiment, the carrier can include surfactants to promote stability and/or distribution of the NELL-1 peptide within the carrier materials such as, but not limited to polyoxyester (e.g. polysorbate 80, polysorbate 20 or Pluronic F-68).

In one embodiment, the carrier can include buffering agents such as, but not limited to glycine, glutamic acid hydrochloride, sodium chloride, guanidine, heparin, glutamic acid hydrochloride, acetic acid, succinic acid, polysorbate, dextran sulfate, sucrose, and amino acids. See for example, U.S. Pat. No. 5,385,887, herein incorporated by reference. In one embodiment, the carrier can include a combination of materials such as those listed above. By way of example, the carrier can a be PLGA/collagen carrier membrane. The membrane can be soaked in a solution including NELL-1 peptide.

An implant can include a substrate formed into the shape of a stent, mesh, pin, screw, plate, or prosthetic joint. An implant can include a substrate that is resorbable, such as a substrate including collagen.

The composition can also include an acceptable carrier to form a pharmacological composition. Acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a carrier, including a physiologically acceptable compound depends, for example, on the route of administration.

The compositions can be administered in a variety of unit dosage forms depending upon the method of administration. For example, unit dosage forms suitable can include powder, or injectable or moldable pastes or suspension.

The compositions of this invention can comprise a pharmaceutically acceptable carrier, such as an aqueous carrier for water-soluble peptides. A variety of carriers can be used, e.g., buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of NELL-1 peptide in these formulations can vary widely, and are selected primarily based on fluid volumes, viscosities, body weight and the like in accordance with the particular mode of administration selected and the patient's needs.

The composition can include the PSC in various density of population. The PSC can have a density from about $1 \times 10^4$ to about $1 \times 10^8$/mL (per 1 mL volume of the composition). In some embodiments, the seeding density can be from about $1 \times 10^4$ to about $1 \times 10^6$, from about $1 \times 10^4$ to about $1 \times 10^5$, from about $1 \times 10^5$ to about $1 \times 10^7$, from about $1 \times 10^5$ to about $1 \times 10^6$, from about $1 \times 10^6$ to about $1 \times 10^7$/ml, or from about $1 \times 10^7$ to about $1 \times 10^8$/ml. Examples of seeding densities can be, e.g., $0.5 \times 10^4$, $1 \times 10^4$, $0.5 \times 10^5$, $1 \times 10^5$, $0.5 \times 10^6$, $1 \times 10^6$, $0.5 \times 10^7$, $1 \times 10^7$, or $1 \times 10^8$/ml.

The formulation can take any dosage form. In some embodiments, it is a powder formulation. In some embodiments, it is a liquid formulation. In some embodiments, it is a semi-solid/semi-liquid formulation, e.g., a gel or paste. In some embodiments, the formulation is an implantable device such as a bone implant. In some embodiments, the formulation is a scaffold.

The dosage regime for NELL-1 can be determined by the clinical indication being addressed, as well as by various patient variables (e.g. weight, age, sex) and clinical presentation (e.g. extent of injury, site of injury, etc.). Generally, the NELL-1 is in a concentration sufficient to cause a PSC to differentiate into cartilage (e.g., cartilage cell or vascular cell) or progenitor cells so as to achieve cartilage regeneration (e.g., cardiomyo regeneration or cardiovascular regeneration).

Dosages of NELL-1 can be determined according to methods known in the art based on type of agent, the disease, and other factors such as age and gender.

In one embodiment, the dosage of NELL-1 factor can be described in terms of an amount per unit area of a composition or per unit weight of a composition. The dosage of NELL-1 generally ranges from 0.001 pg/mm$^2$ to 1 pg/mm$^2$, or more preferably from 0.001 ng/mm$^2$ to 1 ng/mm$^2$, or more preferably from 0.001 µg/mm$^2$ to 1 µg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage of NELL-1 generally ranges from 0.001 pg/ml to 1 pg/ml, or more preferably from 0.001 ng/ml to 1 ng/ml, or more preferably from 0.001 µg/ml to 1 µg/ml, or more preferably from 0.001 mg/ml to 1 mg/ml, or more preferably from 0.001 g/ml to 100 g/ml, with or without a particular carrier or scaffold. In yet another embodiment, the dosage of NELL-1 generally ranges from 0.001 pg/kg to 1 pg/kg, or more preferably from 0.001 ng/kg to 1 ng/kg, or more preferably from 0.001 µg/kg to 1 µg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold.

In some embodiments, the NELL-1 dosage can be described in terms of an amount per kilogram of body weight. For example, for the administration to adult humans, the dosage of NELL-1 can range from about 0.1 µg to about 100 mg per kilogram of body weight. In some embodiments, a suitable dose of a NELL-1 composition for the administration to adult humans is in the range of about 0.001 mg to about 20 mg per kilogram of body weight. In some embodiments, a suitable dose of a NELL-1 composition for the administration to adult humans is in the range of about 0.005 mg to about 10 mg per kilogram of body weight. In some embodiments, a suitable dose of a NELL-1 composition for the administration to adult humans is in the range of about 0.01 mg to about 5 mg per kilogram of body weight. In some embodiments, a suitable dose of a NELL-1 composition for the administration to adult humans is in the range of about 0.05 mg to about 1.0 mg per kilogram of body weight. However, the precise dosage to be therapeutically effective and non-detrimental can be determined by those skilled in the art.

Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

Devices

The composition can be formulated into an injectable or implantable device in any desired form. Some exemplary devices can be for intervertebral disc nucleus replacement, knee meniscus replacement, wrist triangular fibrocartilage replacement, temporomandibular joint replacement, articular cartilage replacement and can consist of, porous scaffold with preformed shape and attachment features to anchor to underlying bone; viscous gel with preformed shape that can be re-shaped by manual manipulation and the cured to new shape by the application of light; or low viscosity liquid that can polymerize in situ. For example, the composition can be formulated into a single mixture (or a simple mixture) for cartilage formation.

In some embodiments, the composition can be formulated into a single device containing specifically designed layers that are tissue-specific, e.g. it may be desirable to have a bone layer to anchor to the hard tissues, and then a cartilage layer immediately adjacent to the bone layer.

In some embodiments, the composition can be formulated into a single mixture allowing multiple tissues formation and self-assembly, such as polymers or monomers with amphiphilic functional groups can self-assemble into macroscopic structures.

In some embodiments, where a device including a composition described herein having a cell(s), the device can be subjected to pre-implantation stimulation. For example, the device can be placed in a mechanical bioreactor with controlled mechanical stimulation (frequency, duty cycle, amplitude, etc.); Frequency in the range of 0.01 Hz to 10,000 Hz, duty cycle above 10%; and amplitude in the range of 0.1-100% strain have reported enhanced cellular function. In some embodiments, the device described herein can be placed in a mechanical bioreactor with controlled microfluidic flow and shear stresses, which arise when at least one flow path or channel has one dimension less than 1 mm. In some embodiments, a device described herein can be implanted in a human being via direct implantation immediately following cell harvesting.

In some embodiments, the composition provided herein can form any of the following examples of devices, which illustrate, but shall not be construed to limit the claimed invention:

an injectable/implantable device containing NELL-1 protein that can be directly injected/implanted into spinal discs to promote cartilage formation;

a disc nucleus replacement device impregnated with NELL-1 factor that can be designed to replace the inner portion of the vertebral disc (the nucleus) or both the inner and outer portion of the disc;

an injectable/implantable device containing NELL-1 protein that can be directly injected into the various joint spaces (e.g., knee, temporomandibular joint, wrist) or implanted arthroscopically or openly into various joint spaces;

an injectable/implantable device containing NELL-1 protein that can be directly injected/implanted into spinal discs to promote cartilage formation;

a disc nucleus replacement device impregnated with NELL-1 protein that is designed to replace the inner portion of the vertebral disc (the nucleus) or both the inner and outer portion of the disc;

an injectable/implantable device containing NELL-1 factor or protein that can be directly injected into the various joint spaces (e.g., knee, temporomandibular joint, wrist) or implanted arthroscopically or openly into various joint spaces;

an injectable/implantable device containing NELL-1 protein that can be directly injected/implanted into spinal discs to promote cartilage formation;

a disc nucleus replacement device impregnated with NELL-1 protein that can be designed to replace the inner portion of the vertebral disc (the nucleus) or both the inner and outer portion of the disc;

an injectable/implantable device of invention that can be directly injected into the various joint spaces (e.g., knee, temporomandibular joint, wrist) or implanted arthroscopically or openly into various joint spaces;

an injectable/implantable device of invention that can be directly injected/implanted into spinal discs to promote cartilage formation;

a disc nucleus replacement device impregnated with NELL-1 protein that is designed to replace the inner portion of the vertebral disc (the nucleus) or both the inner and outer portion of the disc;

an injectable/implantable device of invention that can be directly injected into the various joint spaces (e.g., knee, temporomandibular joint, wrist) or implanted arthroscopically or openly into various joint spaces.

In some embodiments, the device is an ACL/PCL fixation devices or a device that provides for cartilage repair, meniscal cartilage repair, rotator cuff repair, shoulder labrum repair, rotator cuff graft reinforcement device, or nerve conduit repair.

In some embodiments, the device is a suture seeded with the PSC or iPS of invention or that otherwise includes the PSC or iPS of invention. In some embodiments, the suture can comprise a composition of invention. The suture can be resorbable or nonresorbable (see, e.g., Yao et al., J Hand Surg., 2011, 36A:252-258).

Cell Seeding

The formulation can take any desirable form for seeding a population of PSC or iPS. In some embodiments, where the formulation is a scaffold or an implant, the formulation can be porous for seeding the PSC or iPS. The pores in the formulation can have a volume that is capable of accommodating the seeding density of the PSC or iPS.

Seeding of the PSC or IPS can be achieved by well established cell seeding procedures (see, e.g., Undale, et al., Mayo Clin Proc., 84(1):893-902 (2009); Cancedda et al., Biomaterials 28: 4240-4250 (2007); and Marcacci, et al., Tissue Engineering, 13(5):947-955) (2007)) and can vary according to the dosage form of the composition. For example, for liquid formulations, seeding can be readily achieved by placing a population in the formulation. An example of seeding a porous implant or scaffold is described in Wei He, et al., Pericyte-Based Human Tissue Engineered Vascular Grafts, in Biomaterials, 31(32):8235-8244 (2010).

The seeding density for PSC or iPS can vary from about $1 \times 10^4$ to about $1 \times 10^8$/mL (per 1 mL volume of the composition). In some embodiments, the seeding density can be from about $1 \times 10^4$ to about $1 \times 10^6$, from about $1 \times 10^4$ to about $1 \times 10^5$, from about $1 \times 10^5$ to about $1 \times 10^7$, from about $1 \times 10^5$ to about $1 \times 10^6$, from about $1 \times 10^6$ to about $1 \times 10^7$/ml, or from about $1 \times 10^7$ to about $1 \times 10^8$/ml. Examples of seeding densities can be, e.g., $0.5 \times 10^4$, $1 \times 10^4$, $0.5 \times 10^5$, $1 \times 10^5$, $0.5 \times 10^6$, $1 \times 10^6$, $0.5 \times 10^7$, $1 \times 10^7$, or $1 \times 10^8$/ml.

The following describes an example of seeding the PSC or iPS in a scaffold:

Seeding of PSC. A hPSC suspension is seeded into the ES-TIPS PEUU scaffolds via a vacuum rotational seeding device described by Soletti et al., Biomaterials, 27(28):4863-70 (2006). In brief, a scaffold is connected to two coaxial stainless steel tees inside an airtight chamber. The chamber is connected to house vacuum to maintain a negative and constant pressure (−130 mmHg), which induces transmural flow of the cell suspension across the scaffold. A syringe pump infuses the cell suspension ($1 \times 10^6$ cells/mL) at 2.5 mL/min into the manually rotating scaffold to reach $3 \times 10^6$ cells per scaffold within less than 2 min, resulting in a scaffold with uniformly distributed cells. Seeded scaffolds are immediately put into static culture for 3 hours, which is sufficient for cellular attachment (see, e.g., Soletti, et al., Biomaterials, 29(7):825-33 (2008)). Scaffolds are then transferred to a spinner flask with 200 mL medium at 15 rpm stirring for 2 days of culture, after which it was implanted into the rat.

Scaffolds are observed under SEM immediately after seeding. The seeded scaffolds after 2 days' dynamic culture are further assessed for histology (H&E), cellular distribution (F-actin and nuclear staining), and attachment (SEM). For F-actin staining, cryosections are permeabilized (0.1% Triton) for 30 min, blocked (2% BSA) for 30 min and then incubated with Alexa 488-conjugated phalloidin (1:500, Sigma) for 1 hour.

EXAMPLES

The embodiments of the present invention are illustrated by the following set forth examples. All parameters and data do not limit the scope of the embodiments of the invention.
General Methods In vitro efficacy is evaluated by trophic factor production and osteogenic differentiation; in vitro safety by genetic stability; in vivo efficacy and safety by imaging, surgical pathology, histology, immunohistochemistry, and cell tracking studies.

Note, as used in the examples, the terms "optimized" or "opt" are used to designate an embodiment or embodiments that achieve a better result or results under given conditions. These terms shall in no way be construed as the preferred embodiments or best modes of the present invention.
Discussions In the studies described herein, we have developed an adult, perivascular stem cell based PSC+NELL-1 combination product that exceeds the efficacy and safety of current bone regeneration therapies. The studies show that when combined with NELL-1, adipose derived PSC are a safer and more efficacious stem cell to use for bone regeneration.

We have marked and purified to homogeneity two distinct human perivascular cell populations: microvascular pericytes (CD146+CD34−CD45−CD31−) and adventitial cells (CD146−CD34+CD45−CD31−). These cells, just isolated or cultured over the long term, are indistinguishable from conventional MSC—hence the collective term perivascular stem cells or PSC (Crisan, M. et al., Cell Stem Cell 3, 301-13 (2008). PSC are robustly osteogenic in culture and in vivo, migrate actively, stimulate angiogenesis and secrete diverse growth factors (Crisan, 2008; Chen, 2009). We have demonstrated that PSC can be purified in sufficient numbers from fat tissue without the need for culture expansion (Data not shown). Importantly, we have determined that our PSC purification protocol enables the isolation of all multipotent stem cell populations, free of endothelial cells, from all human tissues tested thus far. In summary, advantages of PSC over MSC include: 1—no need for culture (may decrease risks of immunogenicity, infection, and genetic instability (Gad, S.C. Pharmaceutical manufacturing handbook: regulations and quality, p. (John Wiley & Sons, Hoboken, N.J., 2008); Dahl, J. A. et al., Int J Dev Biol 52, 1033-42 (2008)), 2—precise characterization in terms of native tissue localization, phenotype and developmental potential (conversely, MSC are only retrospectively derived from primary, heterogeneous cell cultures), and 3—improved trophic potency [we have determined that PSC secrete 10-20 times more heparin binding epidermal growth factor (HB-EGF) and 3-7 times more basic fibroblast growth factor (FGF) and vascular endothelial growth factor (VEGF) than classically derived adipose tissue and cord blood MSC (Chen, 2009)]. Thus from an FDA regulation perspective, using PSC can facilitate demonstration of consistency in product identity, purity, and potency.

NELL-1 is used to provide PSC or iPS within an osteoinductive environment to promote predictable bone growth. NELL-1 reproducibly induces bone regeneration in various small animals (see, e.g., Cowan, C. M. et al., J Bone Miner Res 22, 918-30 (2007)) and in interbody spinal fusion models in sheep (Lu, S. et al., JBMR 22, S171 (2007)) and non-human primates. The high osteospecificity of NELL-1 derives in part from its direct regulation by Runx2, the master control gene for osteoblast differentiation (Truong, T. et al., J Bone Miner Res 22, 7-18 (2007)). NELL-1 specifically suppresses adipogenesis and peroxisome proliferator activated receptor y (PPARγ) signaling, while promoting B-catenin-dependent Wnt signaling, in bone marrow MSC (Aghaloo, T. et al., Mol Ther 15, 1872-80 (2007)), making this growth factor suitable for aged or osteoporotic individuals where adipogenic differentiation of bone marrow stem cells contributes to the pathogenesis of bone loss (see, e.g., Duque, G., Curr Opin Rheumatol 20, 429-34 (2008)). The studies below show the potent effect, in culture and in vivo, of NELL-1 on purified PSC in terms of osteogenesis promotion.

Osteoinduction Studies

1. Comparison Studies on hPSC Safety/Efficacy with that of hSVF Cells

The studies show that when combined with NELL-1, adipose derived PSC are a safer and more efficacious stem cell source to use for bone regeneration. The studies demonstrate that human PSC are at least as efficient, and possibly superior to total tissue stroma (the adipose tissue SVF in this case) and conventional, in vitro derived MSC in terms of cell viability, purity, stem cell content, trophic factor production, osteogenic differentiation, maintaining genetic stability (tumorigenicity), fate/survival, angiogenesis and osteogenesis.

Methods and Techniques

1—adipose tissue derived PSC (i.e., pericytes and adventitial cells sorted by FACS, mixed but not expanded in vitro) are compared with 2—the non-cultured total stromal vascular fraction (SVF, i.e., total fat, less the adipocytes), 3—the same PSC population as in 1, maintained in culture, and 4—ASC (adipose tissue derived stem cells) derived conventionally from primary long term culture of the SVF, all from the same human lipoaspirate sample. All cultured cells are tested after 1, 4, 8 and 14 passages. To ensure reproducibility, similar studies are performed with several lipoaspirate samples from different donors controlled for age (young vs. old), sex, sample anatomic location, and body mass index. Our tests showed NELL-1 positively affected PSC survival/proliferation and differentiation (data not shown), which is further supported by the examples in FIGS. 10 and 11.

Lipoaspirates, SVF and PSC are isolated per protocol (Crisan, M. et al., Curr Protoc Stem Cell Biol Chapter 2, Unit 2B 2 1-2B 2 13 (2008)). Relative percentages of pericytes (CD146+ NG2+ PDGF-β+ CD34− CD31− CD45−) and adventitial cells (CD146− NG2-PDGF-Rβ— CD34+ CD31− CD45−) are quantified in the SVF, and in the cultured ASC and PSC cell populations. Endothelial cell (CD34+ CD31+ CD45−) numbers are also measured in the SVF and ASC cell fractions, as these cells may inhibit the differentiation of PSC. Initial viability of PSC and SVF fractions recovered from lipoaspirate are determined with DAPI staining and flow cytometry analysis. Cell purity is assessed by comparing FACS results from PSC—pre-cultured or not—, SVF and ASC as well as real time PCR (RT-PCR) analysis of endothelial, hematopoietic, and fibroblast lineage markers. As an approximation of mesenchymal stem cell content, SVF and PSC are seeded at low density to test and quantify their ability to give rise to clonal fibroblast (CFU-F) and osteoblastic (CFU-OB) colonies. To evaluate the maintenance of MSC progenitors over time, CFU-F and CFU-OB assays are performed on cultured PSC and cultured SVF-derived ASC as described (Pittenger, M. F. et al., Science 284, 143-7 (1999)). Production of trophic factors (HB-EGF, VEGF, FGF, and PDGF-BB) by cultured cells is measured using a multiplexed sandwich ELISA assay that allows quantitative measurement, by chemiluminescence, of several proteins per well (Chen, 2009). Significant, measurable amounts of these growth factors are already present at passage one (Chen, 2009), which gives us an approximation of growth factor secretion by non-cultured PSC and total SVF, as compared with longer cultured PSC and ASC. For osteogenic differentiation, PSC (pre-cultured or not), SVF and ASC are cultured in the presence of ascorbic acid and beta-glycerol phosphate. Osteoblastic differentiation is detected quantitatively by real time PCR (Runx2, Osterix, osteopontin, and osteocalcin) (Aghaloo, T. et al., Am J Pathol 169, 903-15 (2006)), alkaline phosphatase (ALP) expression and alizarin red staining (Cowan, C. M. et al., J Bone Miner Res 22, 918-30 (2007)).

Figure 10:
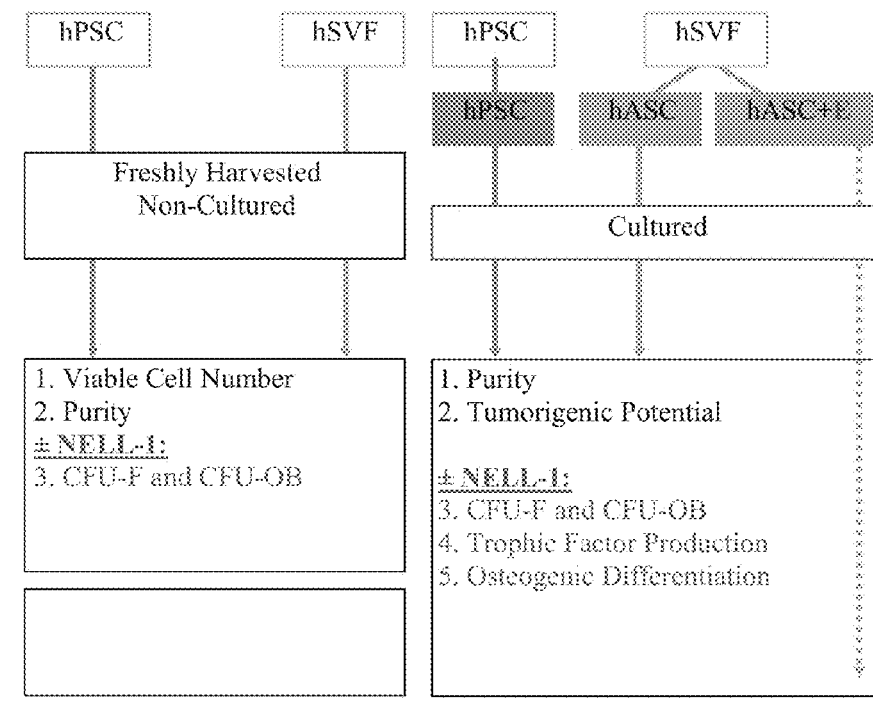
FIG. 10 shows results of in vitro studies on osteogenic differentiation experiments on purified PSC cultured in association (contact co-culture) with endothelial cells.

Another reason to use purified PSC rather than the total SVF fraction as a source of therapeutic osteogenic cells is that endothelial cells negatively regulate the differentiation potential of MSC such as ASC or BMSC (Rajashekhar, G. et al., Stem Cells 26, 2674-81 (2008); Meury, T. et al., J Cell Biochem 98, 992-1006 (2006)) (and our unpublished results). To confirm and document these results, the same osteogenic differentiation experiments are repeated on purified PSC cultured in association (contact co-culture) with endothelial cells (E) sorted from the same fat tissue samples (FIG. 10).

Figure 11:
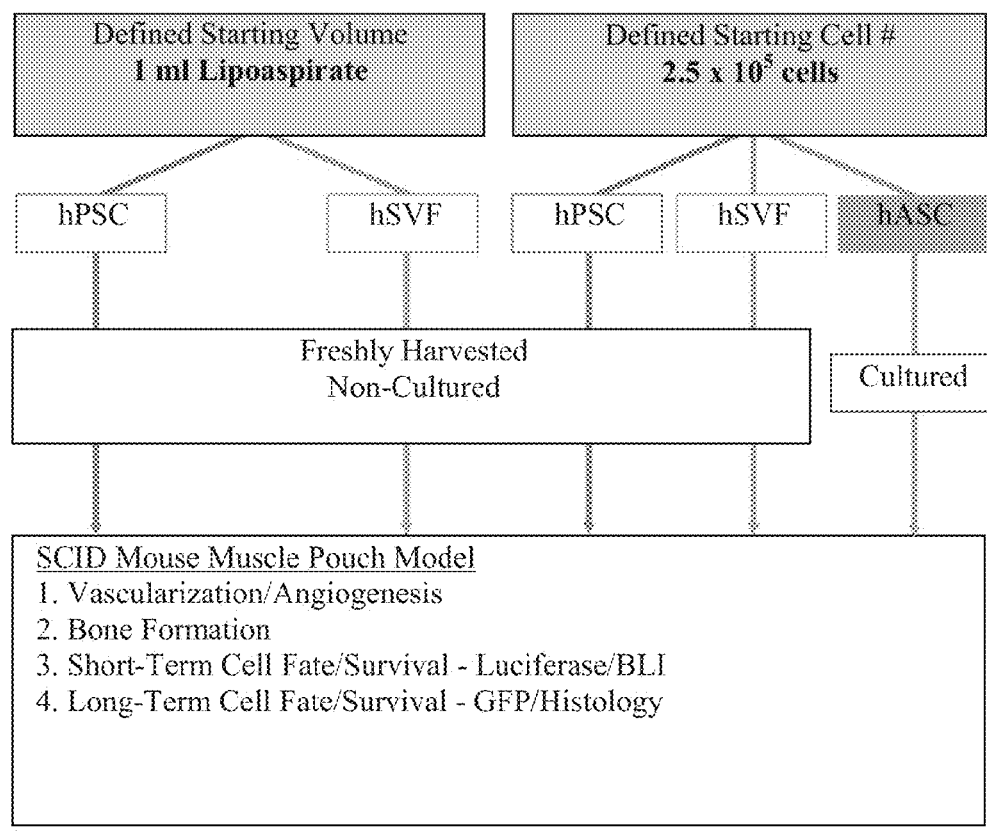
FIG. 11 shows results of in vivo studies on cell fate/survival, angiogenesis, and osteogenesis assessed after implantation in SCID mouse thigh muscle pouch.

To assay tumorigenic potential, cells are first analyzed for anchorage independent growth after plating at various densities in soft agar in proliferation medium. Colonies are counted at 2 and 3 weeks post seeding. In parallel, cells from the different populations to be assayed are seeded on a piece of Gelfoam and implanted into a skeletal muscle pocket in the hind-limb of a SCID mouse. Animals are monitored for tumor formation by physical palpation, eventually sacrificed and analyzed for the presence of tumors (Zheng, B. et al., Nat Biotechnol 25, 1025-34 (2007)). Karyotypes of all cell populations under study are also analyzed on fixed metaphasic chromosomes to detect possible anomalies (Tolar, J. et al., Stem Cells 25, 371-9 (2007)). Cell fate/survival, angiogenesis, and osteogenesis are assessed after implantation in SCID mouse thigh muscle pouch (FIG. 11, Table 2). Cells are labeled [using lentiviral luciferase or green fluorescent protein (GFP)], seeded on acellular allograft bone scaffold±300 µg NELL-1 and implanted bilaterally in mouse biceps femoris (total volume=100 µl/side). Unless otherwise specified, all in vivo studies in this proposal utilize NELL-1 that is lyophilized onto 200-300 µm β-tricalcium phosphate carrier particles (β-TCP) of defined composition and porosity for enhanced biochemical stability (retains bioactivity for up to 3 months when stored at room temperature) and biological efficiency (Li, W. et al., Tissue Eng, 16(9): 2861-2870 (2010)). Both cells isolated from a defined lipoaspirate volume (1 ml) or defined cell numbers ($2.5 \times 10^5$) are tested.

Human cell persistence and migration are tracked using bioluminescence imaging (BLI) and luciferase immunostaining (short term: 1-8 weeks) as well as GFP/histology (long term: 3 months). hPSC mediated vascular ingrowth and bone formation are assessed by histology (hematoxylin-eosin), histomorphometry (Masson trichrome) and immunostaining (vWF, VEGF, BSP, OCN and human MHC Class I). Quantitative bone volume/tissue volume, bone surface area/volume, mineralization density, along with trabecular thickness, number, and separation (Borah, B. et al., JBMR 15, 1786-1797 (2000)) are assessed by high-resolution microCT (SkyScan™; Kontich, Belgium) and analyses are performed using Skyscan™ CT Analyzer software (Zhang, X. et al., J Clin Invest 110, 861-70. (2002)).

regeneration models. These studies show that the hPSC+ NELL-1 product is more or as efficacious and safe as BMP2 or autologous bone graft.

Methods and Techniques

For initial formulation of the therapeutic product, systematic studies on hPSC density ($PSC^{OPT}$) and NELL-1 dose ($NELL-1^{OPT}$) are performed. First, luciferase tagged hPSC are implanted in a biocompatible carrier at three densities±NELL-1 (300 µg total dose; 3.0 mg/ml) in SCID mice (Table 3).

TABLE 2

| SCID Mouse Muscle Pouch Model | | | | | | | | |
|---|---|---|---|---|---|---|---|---|
| DEFINED 1 ml | | | SACRIFICE | | | | | |
| LIPOASPIRATE VOLUME | | | 1 wk | 2 wk | 3 wk | 4 wk | 8 wk | 3 mo |
| Cell | Lentiviral | NELL-1 | Bioluminescence Imaging (BLI) | | | | | GFP |
| hPSC | Luciferase | + | 4 mice | 4 mice | 4 mice | 4 mice | 4 mice | |
|  |  | − | 4 mice | 4 mice | 4 mice | 4 mice | 4 mice | |
|  | GFP | + |  |  |  |  |  | 4 mice |
|  |  | − |  |  |  |  |  | 4 mice |
| hSVF | Luciferase | + | 4 mice | 4 mice | 4 mice | 4 mice | 4 mice | |
|  |  | − | 4 mice | 4 mice | 4 mice | 4 mice | 4 mice | |
|  | GFP | + |  |  |  |  |  | 4 mice |
|  |  | − |  |  |  |  |  | 4 mice |
| DEFINED 2.5 × 105 CELL NUMBER | | | | | | | | |
| hPSC | Luciferase | + | 4 mice | 4 mice | 4 mice | 4 mice | 4 mice | |
|  |  | − | 4 mice | 4 mice | 4 mice | 4 mice | 4 mice | |
|  | GFP | + |  |  |  |  |  | 4 mice |
|  |  | − |  |  |  |  |  | 4 mice |
| hSVF | Luciferase | + | 4 mice | 4 mice | 4 mice | 4 mice | 4 mice | |
|  |  | − | 4 mice | 4 mice | 4 mice | 4 mice | 4 mice | |
|  | GFP | + |  |  |  |  |  | 4 mice |
|  |  | − |  |  |  |  |  | 4 mice |
| Cultured hACS | Luciferase | + | 4 mice | 4 mice | 4 mice | 4 mice | 4 mice | |
|  |  | − | 4 mice | 4 mice | 4 mice | 4 mice | 4 mice | |
|  | GFP | + |  |  |  |  |  | 4 mice |
|  |  | − |  |  |  |  |  | 4 mice |
| Total Animals Used | | | 240 Mice (2 implants per animal) | | | | | |

If in some embodiments, quantitative assessment of PSC vs. ASC is required in terms of developmental potential, differentiation into myotubes can be tested in vitro as previously performed (Zheng, 2007). The exemplary cell seeding density ($2.5×10^5/100$ µl) and NELL-1 dose (100-300 µg; 1.0-3.0 mg/ml) are identical to those used in our test data demonstrating successful cell survival, bone formation, and vascular ingrowth (data not shown). We have also determined that 100 ml SVF yields ~$2.3×10^7$ cells, of which ~24% (~$1.2×10^7$ cells) are PSC (Table 1). Thus, the use of "1 ml" as the "defined lipoaspirate volume" is within range to provide sufficient cell numbers (~$10^5$) for osteogenesis. If needed, in some embodiments, we can alter the defined volume, cell number, or NELL-1 dose to further enhance bone formation.

2. Studies on hPSC+NELL-1 Formulations in Rodent Bone Formation

Based on safety and efficacy endpoints, the hPSC+ NELL-1 formulation is further compared with BMP2+Helistat® collagen sponge (INFUSE® Bone Graft) and gold standard "autologous" bone graft for safety and efficacy in normal and impaired [e.g., ovariectomized (OVX)] bone

TABLE 3

| SCID Mouse Muscle Pouch Model (100 µl Total Volume) | | | | | | |
|---|---|---|---|---|---|---|
| DETERMINE OPTIMAL | | | SACRIFICE | | | |
| CELL # ($hPSC^{OPT}$) FOR SF | | | 1 wk | 2 wk | 3 wk | 4 wk |
| Cells | Cell # | NELL-1 | Bioluminescence Imaging | | | |
| Fresh hPSC (Luciferase tagged) | $2.5 × 10^4$ | + | 4 mice | 4 mice | 4 mice | 4 mice |
|  |  | − | 4 mice | 4 mice | 4 mice | 4 mice |
|  | $2.5 × 10^5$ | + | Performed in Aim 1A | | | |
|  |  | − |  |  |  |  |
|  | $2.5 × 10^6$ | + | 4 mice | 4 mice | 4 mice | 4 mice |
|  |  | − | 4 mice | 4 mice | 4 mice | 4 mice |
|  |  | − | 4 mice | 4 mice | 4 mice | 4 mice |
| Total Animal Used | | | 64 Mice (2 implants per animal) | | | |

The effect of NELL-1 on hPSC persistence, hPSC mediated vascular ingrowth and bone formation at the various densities is assessed. The hPSC density demonstrating the most optimal BLI signals and bone growth are designated $hPSC^{OPT}$. Second, we test GFP tagged $hPSC^{OPT}$ at the maximum concentration of 3.0 mg/ml, as well as 1.5 and 0.75 mg/ml in an athymic rat SF model that normally fuses at 4 weeks with non-cell based NELL-1 (Table 4).

TABLE 4

| DETERMINE OPTIMAL NELL-1 DOSE (NELL-1$^{OPT}$) | | | Athymic Rate Spine Fusion (SF) Model (300 μl) | | |
|---|---|---|---|---|---|
| Cells | Total Dose NELL-1 | Concentration NELL-1 | Total Volume SACRIFICE | | |
| | | | 2 wk | 3 wk | 4 wk |
| Fresh hPSC$^{OPT}$ (GFP tagged) | 900 μg | 3.0 mg/ml | 4 rats | 4 rats | 4 rats |
| | 450 μg | 1.5 mg/ml | 4 rats | 4 rats | 4 rats |
| | 225 μg | 0.75 mg/ml | 4 rats | 4 rats | 4 rats |
| | No NELL-1 Control) | | 4 rats | 4 rats | 4 rats |
| No hPSC (Control) | 900 μg | 3.0 mg/ml | 4 rats | 4 rats | 4 rats |
| Total Animals Used | | | 60 Rats (1 SF/animal) | | |

The NELL-1 dose demonstrating the most vascularization and bone growth with hPSC are designated NELL-1$^{OPT}$. The optimized formulation for spine fusion efficacy (PSC$^{OPT}$+ NELL-1$^{OPT}$) are directly compared to BMP2/collagen (INFUSE® Bone Graft) and fresh rat bone graft in normal or OVX (Lelovas, P. P. et al., Comp Med 58, 424-30 (2008)) skeletally mature, athymic rats (Table 5). Because syngeneic athymic rats are not available, we use allogeneic athymic donors.

TABLE 5

| Compare hPSC$^{OPT}$ + NELL-1$^{OPT}$ WITH CURRENT THERAPHY | Athymic Rat Spine Fusion (SF) Model (300 μl Total Volume) | | | | | |
|---|---|---|---|---|---|---|
| | SACRIFICE | | | | | |
| | Normal Rat | | | OVX Rat | | |
| Treatment Groups | 2 wk | 3 wk | 4 wk | 4 wk | 6 wk | 8 wk |
| Fresh hPSC$^{OPT}$ + NELL-1$^{OPT}$ | 6 rats | 6 rats | 6 rats | 6 rats | 6 rats | 6 rats |
| BMP2 + Collagen Sponge | 6 rats | 6 rats | 6 rats | 6 rats | 6 rats | 6 rats |
| Fresh Bone Graft | 6 rats | 6 rats | 6 rats | 6 rats | 6 rats | 6 rats |
| Total Animals Used | 108 Rats (1 SF per animal | | | | | |

Efficacy and safety are evaluated by imaging, surgical pathology, histology, immunohistochemistry, and cell tracking studies as described above. Biomechanical testing is also performed. Anti-murine antibodies (from FACS) or anti-NELL-1 are detected by ELISA. Immunostaining for osteoblastic, chondrogenic, and adipogenic cell markers such as RUNX2, SOX9, collagen II and X, or PPARγ is performed. Because both OVX and BMP2 promote osteoclastogenesis (Irie, K. et al., J Bone Miner Metab 21, 363-9 (2003)), tartrate-resistant acid phosphatase (TRAP) staining is performed to assess osteoclast activity (a potential safety issue as excessive osteoclast activity can cause vertebral subsidence). Bone mineral loss in OVX animals is assessed by dual x-ray absorptiometry (DEXA).

Figure 7:
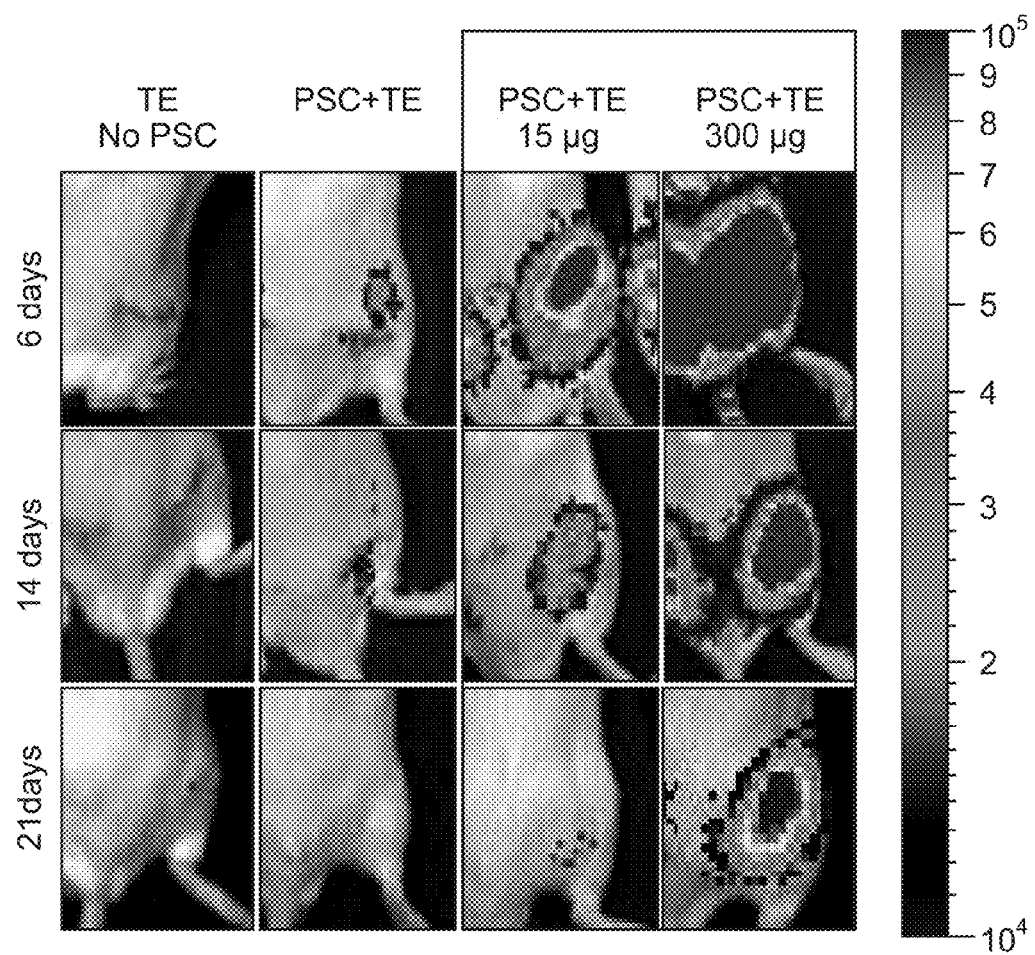
FIG. 7 shows bioluminescence imaging of implanted human PSC. SCID mice (n=4 in each group) were implanted intramuscularly with TE® ±2.5×10$^5$ PSC±15 or 300 µg NELL-1/TCP in 100 µl total volume. No luciferase detected in PSC-free controls.
Figures 8A, 8B, 8C, 8D:
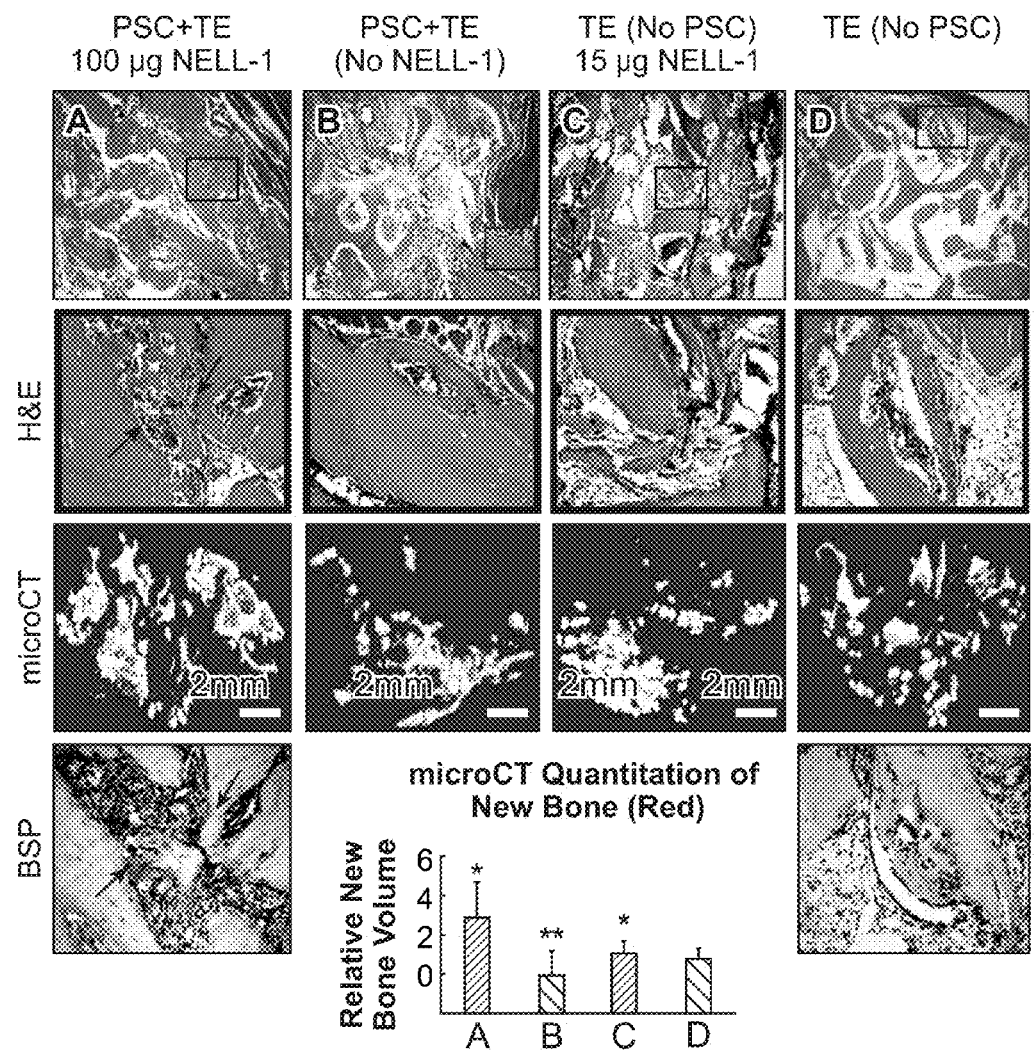
FIGS. 8A-8D show results on PSC+NELL-1 at 4 weeks post implant. SCID mice were implanted with TE®±2.5×105 PSC±NELL-1/TCP in 100 µl volume. Relative to TE® (D), note the abundant new bone formation in the PSC+NELL-1 group (A) (red areas in microCT) with increased bone sialoprotein (BSP) staining (arrows) and bony consolidation of the TE® particles and marrow space formation (H&E, arrows). Note the sparse cellularity and less active bone formation in the TE® only group (D). =P<0.05 higher vs. TE® only group (D); =P<0.05 lower vs. TE® only group (D).

In some embodiments, cell seeding densities and NELL-1 doses can be varied to achieve hPSC osteoinduction. Exemplary hPSC densities are from $2.5 \times 10^4$ to $10^6/100$ μl and are within range of published reports demonstrating successful MSC-mediated bone formation with larger implant volumes and/or diffusion distance in sheep (see, e.g., Kon, E. et al., J Biomed Mater Res 49, 328-37 (2000)), goat (Zhu, L. et al., Tissue Eng 12, 423-33 (2006)) and humans (Marcacci, M. et al., Tissue Eng 13, 947-55 (2007)). With respect to NELL-1 dosing, NELL-1 at 3.0 or 1.0 mg/ml more effectively stimulated hPSC survival or bone formation, respectively, in SCID mouse muscle pouch than 0.15 mg/ml (FIGS. 7 and 8). Meanwhile, non-cell based NELL-1 induces non-human primate spinal interbody fusion at a dose of 1.7 mg/ml in 400 μl (total dose=680 μg) at 3 months (not shown). An example of NELL-1 formulations, lyophilized NELL-1 on β-TCP carrier, provides a 40% burst release in the initial 24 hours followed by a 45% slow release over two weeks (Li, 2010) and has successfully induced spine fusion in rat, sheep, and NHP models. However, non-cell based NELL-1 relies on NELL-1 diffusion from the scaffold or cell migration to the scaffold to come in contact with NELL-1. In the present invention, because the hPSC are in closer proximity to NELL-1, initial NELL-1 burst release is not required and fusion may be achieved with the use of non-burst release carriers and reduced NELL-1 dose.

3. Studies on cPSC+NELL-1 Efficacy in Bone Formation in Comparison with BMP2 or Autologous Bone Graft The studies show that that the cPSC+NELL-1 product is more or as efficacious and safe as BMP2 or autologous bone graft.

Methods and Techniques

A human device previously used in sheep and monkey spine studies is implanted in a canine model of spine fusion. There is a species-specific dose escalation to achieve fusion using BMP2 (McKay, W. Science-based assessment: Accelerating product development of combination medical devices. in NMAB Roundtable on Biomedical Engineering Materials and Applications (Washington, D.C., 2003)) and NELL-1. Since dog and sheep have similar dose ranges, the 0.6 mg/ml NELL-1 dose that was effective in sheep is used. Spine fusion efficacy of non cell based NELL-1 in dogs at 0.6 mg/ml+acellular allograft bone carrier with 2 lumbar implants per animal (N=6 NELL-1 and N=6 No NELL-1 control implants) can be performed as control. GFP tagged cPSC at 5-fold above and 5-fold below the hPSC$^{OPT}$ density with two different NELL-1 doses and saline controls (N=4 in each group; total N=36 implants) can be tested. The GFP tagged cPSC$^{OPT}$+NELL-1$^{OPT}$ can then be tested with BMP2 (INFUSE® Bone Graft) and autograft bone (N=6 in each group; total N=18 implants).

4. Examples of Osteoinduction Studies

Isolation of 1-Perivascular Stem Cells

Figure 2:
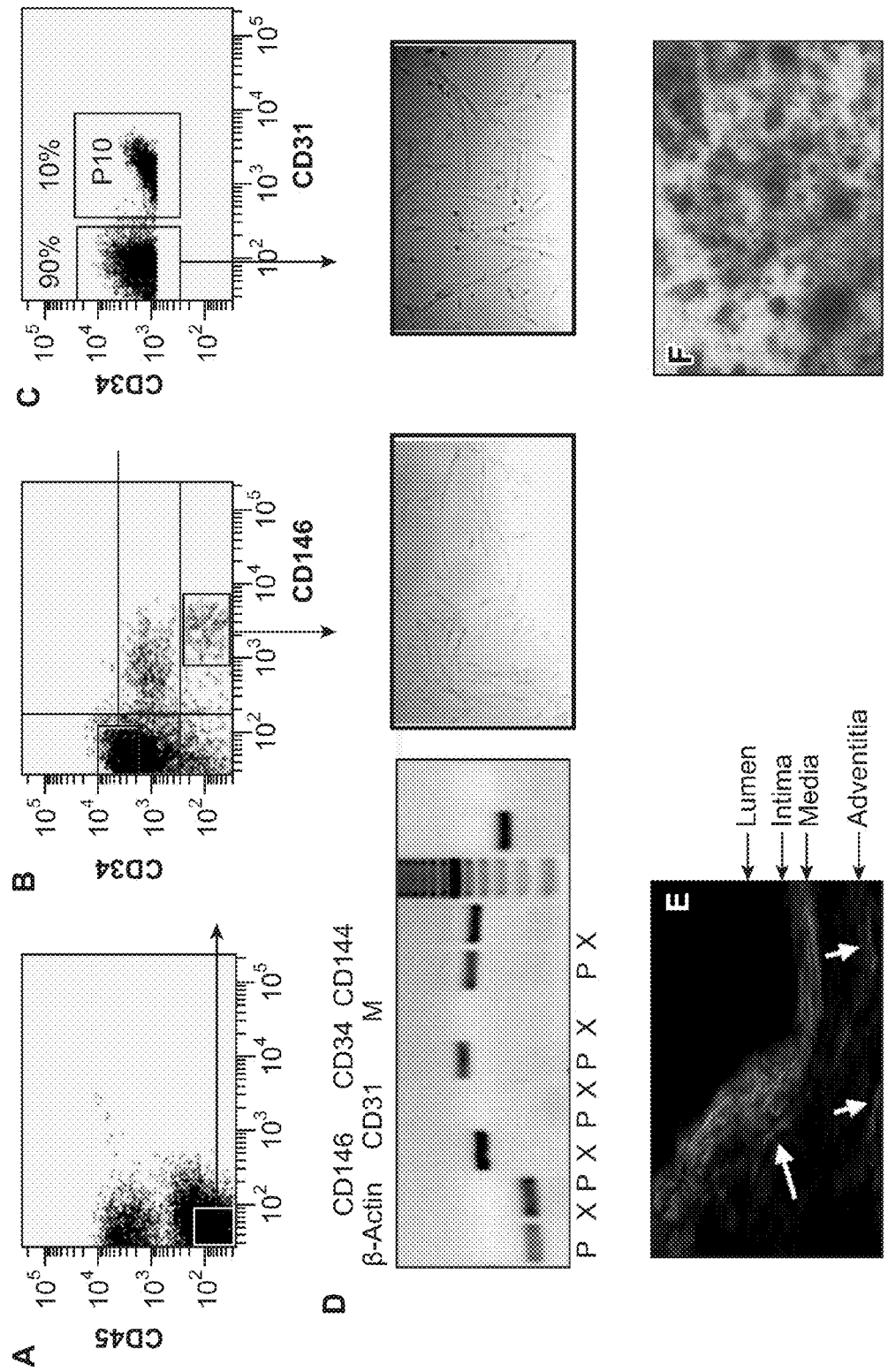
FIGS. 2A-2F show adventitial MSC. (A,B) Pericytes were sorted from adipose tissue (red), as well as CD146−CD34$^{hi}$ cells (green), also endowed with stem cell potential. (C) CD146−CD34$^{high}$ cells were further divided into CD31+ and CD31− cells, only the latter gave rise to MSC. Sorted CD146−CD34$^{high}$ CD31− cells (x) are not contaminated by endothelial cells or pericytes (D). (E) CD146−CD34$^{hi}$ CD31− cells (arrows) are all localized in the tunica adventitia of larger blood vessels (CD34 in red). (F) Purified adventitial MSC are osteogenic in vitro (alizarin red staining)
Figures 3A, 3B, 3C, 3D, 3E, 3F:
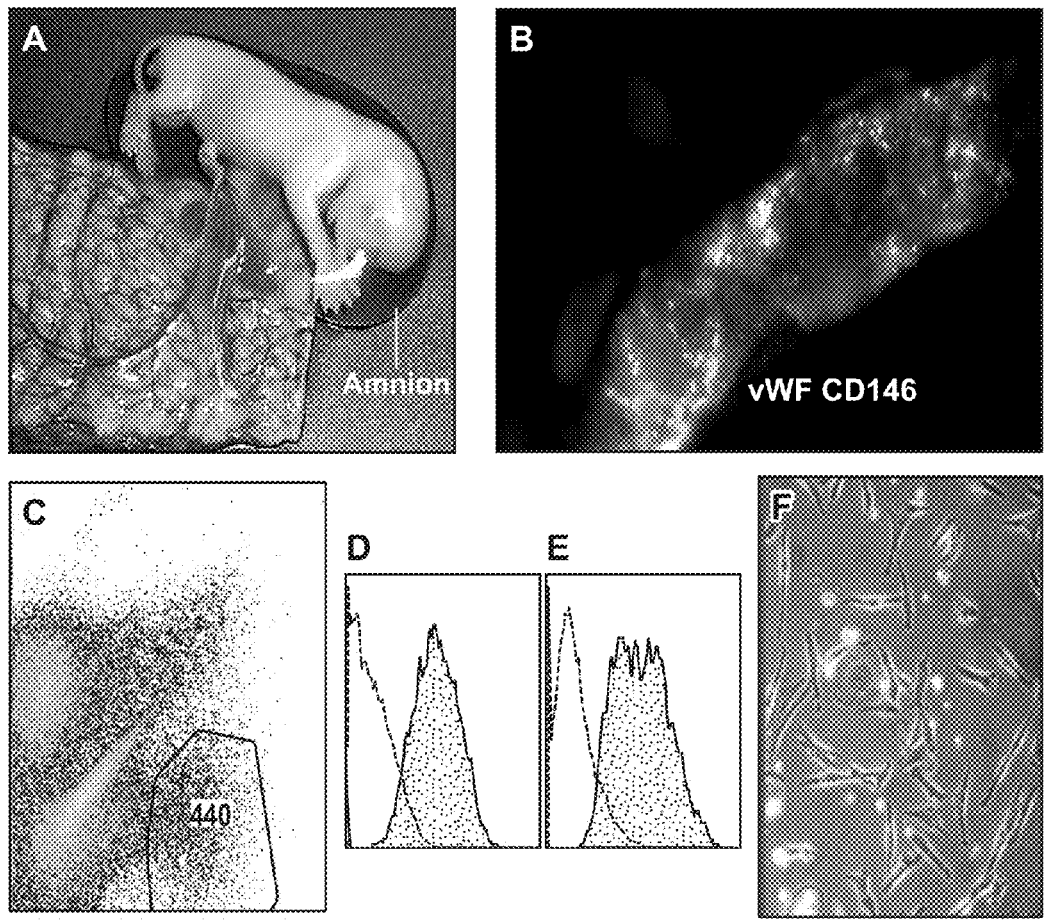
FIGS. 3A-3F show dog pericytes. The placenta (A) was used as a source of canine pericytes. vWF+ endothelial cells are encircled by CD146+ pericytes (B). As for human cells, canine pericytes were sorted as CD146+CD34− cells (gate in C; compare with FIG. 1E), coexpress CD90 (D) and CD44 (E) and were established in long-term culture (F)

We have prospectively identified vascular pericytes in multiple human organs and shown that these cells are mesodermal progenitors that give rise to MSC in culture (Crisan, 2008; Crisan, M. et al. Methods Cell Biol 86, 295-309 (2008). Pericytes can differentiate into cartilage, fat, skeletal muscle and bone cells (FIGS. 1A-1G), but also secrete multiple growth factors, which likely explains in part their robust regenerative potential (Chen, 2009). However, non-pericyte cells (outside the red gate in FIG. 1E), were also found to include MSC progenitors. Further partition revealed that this MSC potential is confined within CD34high CD31− (non-endothelial) cells (FIG. 2C), all found in the tunica adventitia of arteries and veins (FIG. 2E). Sorted adventitial MSC differentiate in culture into cartilage, bone (FIG. 2F) and fat cells, and into myofibers after injection into the SCID mouse muscle.

In summary, two categories of perivascular cells, pericytes and adventitial cells, named collectively perivascular stem cells (PSC), account for the origin of MSC in all human tissues tested. PSC natively express MSC markers, are multipotent, and upon culture exhibit the shape, growth characteristics, migratory properties, developmental potential and functions, including immunomodulation and hematopoiesis support, of conventional MSC. Importantly, PSC contain the whole potential to give rise to MSC.

Several antibodies to markers used to characterize human PSC (vWF, CD34, CD44, CD90, CD146 and NG2) cross-react with the canine homologs. We have characterized pericytes in the dog placenta; FACS purification and culture of these cells revealed characteristics similar to those of human pericytes (FIGS. 3A-3F).

PSC Yields from Lipoaspirates

Our data on PSC yields from the stromal vascular fraction (SVF) of human lipoaspirates agrees with published adipose derived stem cell (ASC) yields assessed by the CFU-F assay (~$10^6$ stem cells/100 ml) (see, e.g., Meliga, E. et al., Cell Transplant 16, 963-70 (2007)) (Table 1). BMSC seeding densities in the $2.5 \times 10^5$ to $10^7$/ml range successfully regenerated bone in large animals and humans (see, e.g., Zhu, 2006; Marcacci, M. et al., Tissue Eng 13, 947-55 (2007)). With typical cosmetic lipoaspirate volumes of 2L (Fraser, J. K. et al., Methods Mol Biol 449, 59-67 (2008)), containing at least $10^6$ viable PSC/100 ml, clinically relevant PSC numbers are readily obtained without culture. Notably, cell viability is higher in PSC than total SVF populations. Thus, sorted PSC should be advantaged over total SVF implants because all non-viable cells are excluded.

TABLE 1

| | Per 100 cc Lipoaspirate | | |
| --- | --- | --- | --- |
| # Total SCF cells | # Viable Cells in SCF | # PSC in SVF | # Viable Cells in PSC |
| $5.0 \pm 2.5 \times 10^7$ | $\sim 2.3 \times 10^7$ (46% ± 4.7%) | $\sim 1.2 \times 10^7$ (24% ± 3.5%) | $\sim 0.8 \times 10^7$ (67% ± 18%) |

NELL-1, an Osteospecific, Osteoinductive Growth Factor

Non-Cell Based Bone Regeneration: NELL-1+allograft reproducibly induced bone regeneration in various small animals (see, e.g., Aghaloo, 2006) as well as in interbody spinal fusion in sheep (Lu, S. et al., JBMR 22, S171 (2007)) and monkeys (not shown). In sheep, NELL-1 in an allograft bone scaffold achieves comparable fusion as the BMP2 (IN-FUSE®) group without the cyst formation seen with BMP2 (not shown).

NELL-1 Inhibits Adipogenesis: NELL-1 significantly reduces endogenous and BMP2 induced expression of the major adipogenic transcription factors (Moerman, E. J. et al., Aging Cell 3, 379-89 (2004)) PPARγ and CCAAT/enhancer binding protein in primary rat BMSCs (not shown). In addition, NELL-1 markedly induces osteoblastogenesis and suppresses BMP2 induced adipogenesis in implanted goat BMSC (Aghaloo, T. et a, Mol Ther 15, 1872-80 (2007)).

Figure 4:
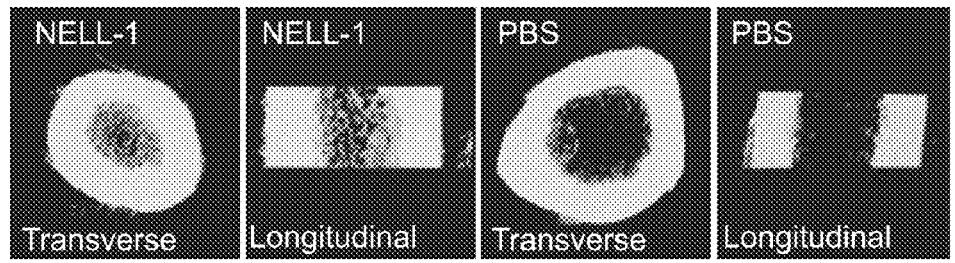
FIG. 4 shows 2 week microCT sections of rat femur. 200 µg NELL-1/TCP, or saline/TCP (control) were injected through a trepanation defect into the rat femur.

NELL-1 Effects on Stem Cells In Situ: NELL-1 significantly increased the number of Stro-1+ cells (MSC related bone marrow stromal cells (Gronthos, S. et al., Blood 84, 4164-73 (1994))) and bone sialoprotein (BSP, an osteoblast marker) expression in rat vertebral bodies (not shown). Accordingly, direct NELL-1/β-TCP carrier injection into the rat femur increases bone volume and marrow density (FIG. 4).

Figure 5:
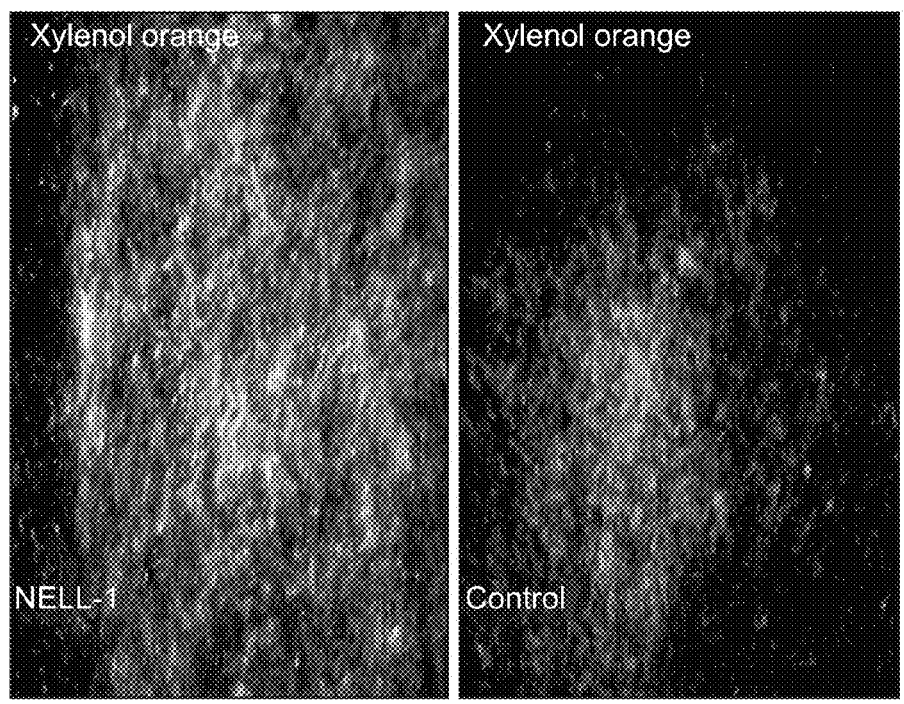
FIG. 5 shows NELL-1 increases human PSC mineralization. PSC were cultured for 9 days±300 ng/ml NELL-1, then stained with xylenol orange fluorochrome.

NELL-1 Effects on PSC In Vitro: When added to PSC under osteogenic conditions NELL-1, 1—significantly increased xylenol orange uptake (a mineralization marker) (FIG. 5) and 2—also significantly increased mRNA levels of the osteoblastic cell markers RUNX2, osterix (OSX), and osteocalcin (OCN), decreased PPARγ, and increased VEGF (not shown). NELL-1 thus potently promotes PSC osteogenic and angiogenic activities.

The PSC+NELL-1 Development Candidate—Comparison with Trinity® Evolution™ (TE®)

Figure 6:
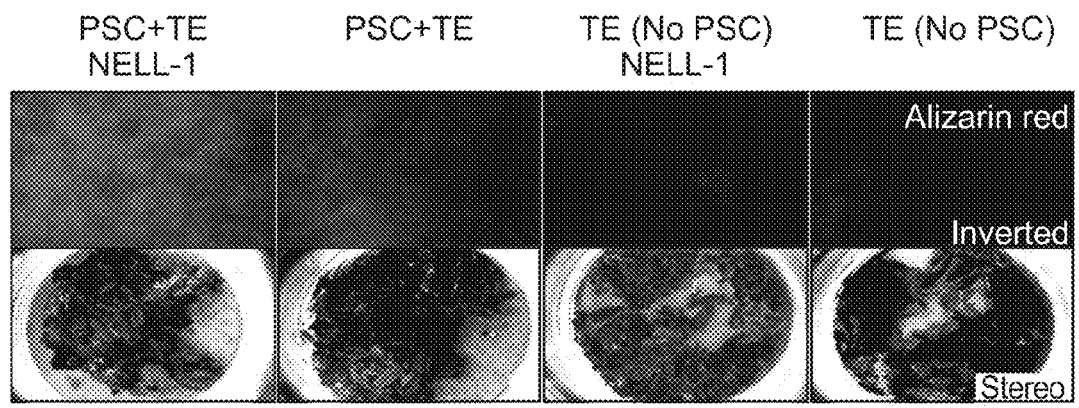
FIG. 6 shows In vitro mineralization of PSC+NELL-1 on TE®. 100 µl of TE® ±300 ng/ml NELL-1 or TE® loaded with 2.5×10$^5$ PSC±300 ng/ml NELL-1 were placed in 24-well plate inserts under osteogenic conditions for 12 days. Mineralization (alizarin red) assessed using inverted (top) or stereo (bottom) fluorescence microscopy.
Figures 9A, 9B, 9C, 9D, 9E, 9F:
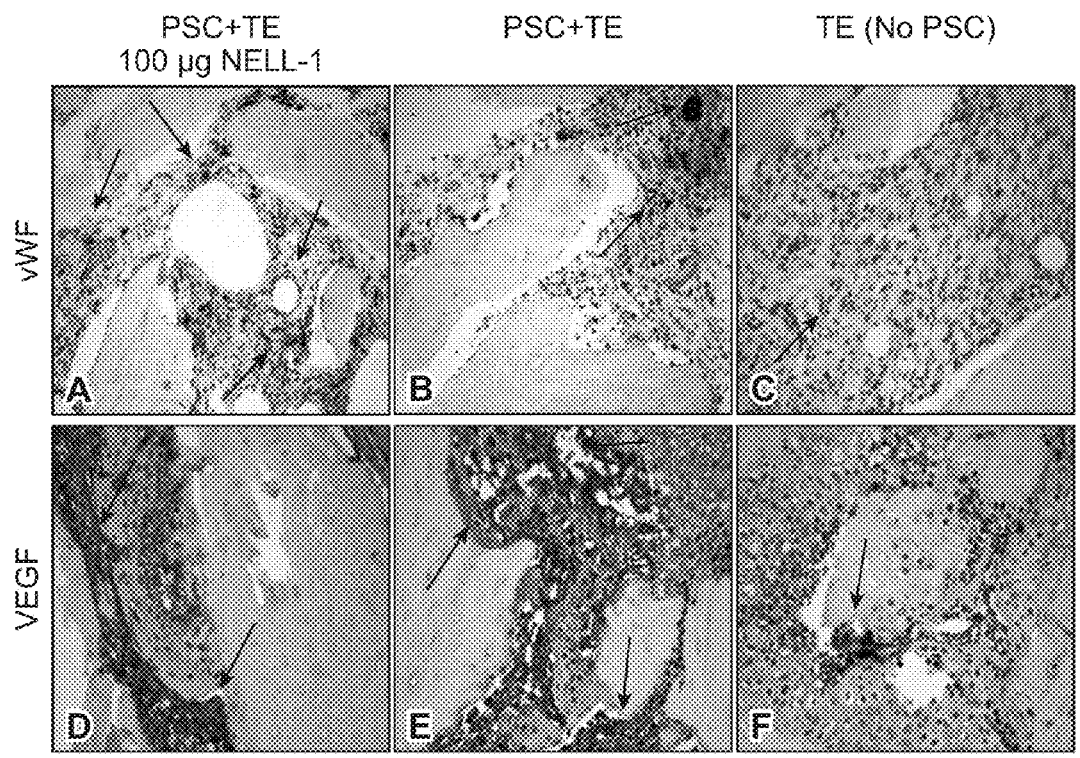
FIG. 9 shows results on angiogenesis in PSC+NELL-1 grafts. SCID mice were implanted per FIG. 8. Immunostaining of 1 week (A-C) and 2 week (D-F) specimens show increased endothelial vWF (A,B-red arrows) and significantly increased VEGF (D,E-yellow arrows) in PSC groups relative to TE®. Anti-human MHC I (H300) staining was also increased in PSC groups, indicating persistence of PSC (not shown).

TE® is a FDA-regulated, cryopreserved allograft bone containing "viable adult stem cells and osteoprogenitor cells" (Bueno, E. M. & Glowacki, Nat Rev Rheumatol 5, 685-97 (2009)). We investigated the osteogenic properties of TE® alone compared to TE® used as a scaffold for PSC, NELL-1, or PSC+NELL-1. When cultured in osteogenic medium, minimal mineralization was seen in TE® or TE® +NELL-1, indicating that TE® contains few osteogenic cells (FIG. 6). In contrast, introduction of PSC increased mineralization, which was further increased by PSC+NELL-1, indicating that adequate numbers of appropriate stem cells (PSC) and NELL-1 are required for maximal mineralization (FIG. 6). Moreover, NELL-1 applied to luciferase tagged PSC+TE® implanted in SCID mouse muscle significantly increased luciferase intensity (FIG. 7); thus NELL-1 promotes PSC survival and/or proliferation. Histological and microCT examination of the SCID mouse implant groups revealed the least bone formation in the TE® and, interestingly, in the PSC+TE® groups (suggesting that NELL-1 is indeed important for in vivo PSC survival or activity) (FIG. 8). Notably, at 4 weeks the PSC+TE® +NELL group exhibited the most bone formation as well as marked BSP expression in a NELL-1 dose-dependent fashion (FIG. 8). Relative to TE®, PSC+TE® induced significantly more endothelial vWF staining in granulation tissue at one week (not shown) and markedly increased VEGF expression at 2 weeks with the effect further augmented by NELL-1 (FIG. 9). PSC are therefore angiogenic, trophic, and osteogenic in the presence of NELL-1. Tagged PSC were still visible at 4 weeks in areas of active mineral deposition and along vessels (not shown). In summary, these data show that i) PSC mineralize and form bone under appropriate environments, ii) NELL-1 is a potent osteospecific, osteoinductive molecule that promotes stem cell function while inhibiting adipogenesis, iii) NELL-1 increases PSC proliferation and/or survival, and iv) PSC+ NELL-1+TE® forms more bone than TE® alone or TE® +PSC. Overall, these data demonstrate the usability and efficacy of PSC+NELL-1 to promote bone formation and vascular ingrowth.

Summary

From our data, we have developed methods to extract adequate quantities of human PSC (hPSC) from lipoaspirate to support cell-based tissue engineering without ex vivo expansion. We have documented hPSC identity, purity and potency (Crisan, 2008; Crisan, M. et al., Curr Protoc Stem Cell Biol Chapter 2, Unit 2B 2 1-2B 2 13 (2008)), and demonstrated the trophic, immunomodulatory, hematopoiesis supporting, angiogenic and osteogenic potentials of hPSC[1-4] (and unpublished results). Importantly, we show superior bone forming efficacy with hPSC+NELL-1 relative to hPSC or NELL-1 alone. Because NELL-1 is currently at the pre-IDE/IND stage for a non-cell based lumbar spinal fusion indication, we have already developed cGMP compliant NELL-1 manufacturing and detailed the mode of action data on NELL-1 osteoinductivity and NELL-1 release data from various 510 (k) approved biocompatible materials for bone regeneration. Therefore, we believe that starting IND-enabling studies in three years is realistic. The seven subaims in this proposal are designed to achieve five milestones needed (interspersed at months 9, 18, and 36) before starting IND-enabling studies.

Example 2

Isolation of Adventitia PSC from Liposuction Aspirate

SVF Isolation from Liposuction Aspirate.

Liposuction aspirate was washed with an equal volume of PBS and centrifuged for 10 minutes at 400×g. After centrifugation, the top layer of the preparation, representing the tissue fraction containing the SVF, was collected and further washed in PBS. The tissue fraction was then enzymatically processed by addition of an equal volume of digestion solution (DMEM, collagenase II 1 mg/ml, DNAse 10 µg/ml, 1% Pen-Strepto, 3% BSA) and incubation for 45 minutes at 37 C under agitation (250rpm). The enzymatic digestion was stopped after addition of PBS 5 mM EDTA and the solution was filtered through 100 µm cell strainer. After two washes in PBS 5 mM EDTA and centrifugation at 400×g for 10 minutes, the supernatant containing adipocytes was discarded and the pellet was resuspended in 10 ml red blood cell lysis buffer for 10 minutes at room temperature. The suspension was washed in PBS 5 mM EDTA and centrifuged at 400×g for 10 min. The pellet containing the SVF was resuspended in DMEM 10% FBS prior to cell count, culture and staining with specific antibodies for the purification of PSC via FACS sorting.

SVF Culture and CFU-F Assay

Conventional MSC-like adipose stem cells (ASC) was isolated by plating $10^7$ unfractionated SVF cells per well in a 6 multiwell plate. CFU-F assay was performed for the determination of the frequency of ASC by limiting dilution of total unfractionated SVF cell plated at the increasing density of $10^2$ to $10^6$ cells per well in a 6 multiwell plate. After 2 weeks of culture, plates were stained with May Grumwald/Giemsa and the number of colonies was scored.

Detection of PSC within the Liposuction-Derived SVF

Three hundred thousand SVF cells were washed and re-suspended in 100 µl of PBS before incubation at 4 C for 20 minutes with DAPI for the exclusion of dead cells and with the following antibodies: CD45,CD34,CD31,CD146. Cells were then washed and resuspended in PBS prior to flow cytometry analysis. After exclusion of dead cells and CD45+ hematopoietic cells, PSC are identified as CD146+CD34− pericytes and CD34+CD31−CD146− adventitial cells. Endothelial cells are instead defined as CD34+CD146+ CD31+ cells. The same staining procedure was used for the isolation of PSC via FACS sorting. Purified PSC were resuspended in EGM2 medium and plated in 0.2% gelatin coated wells at the density of $2\times10^4$ cells per $cm^2$. CFU-F assay were performed as above described.

Example 3

Osteogenic Studies on Pericytes and NELL-1

Figure 12:
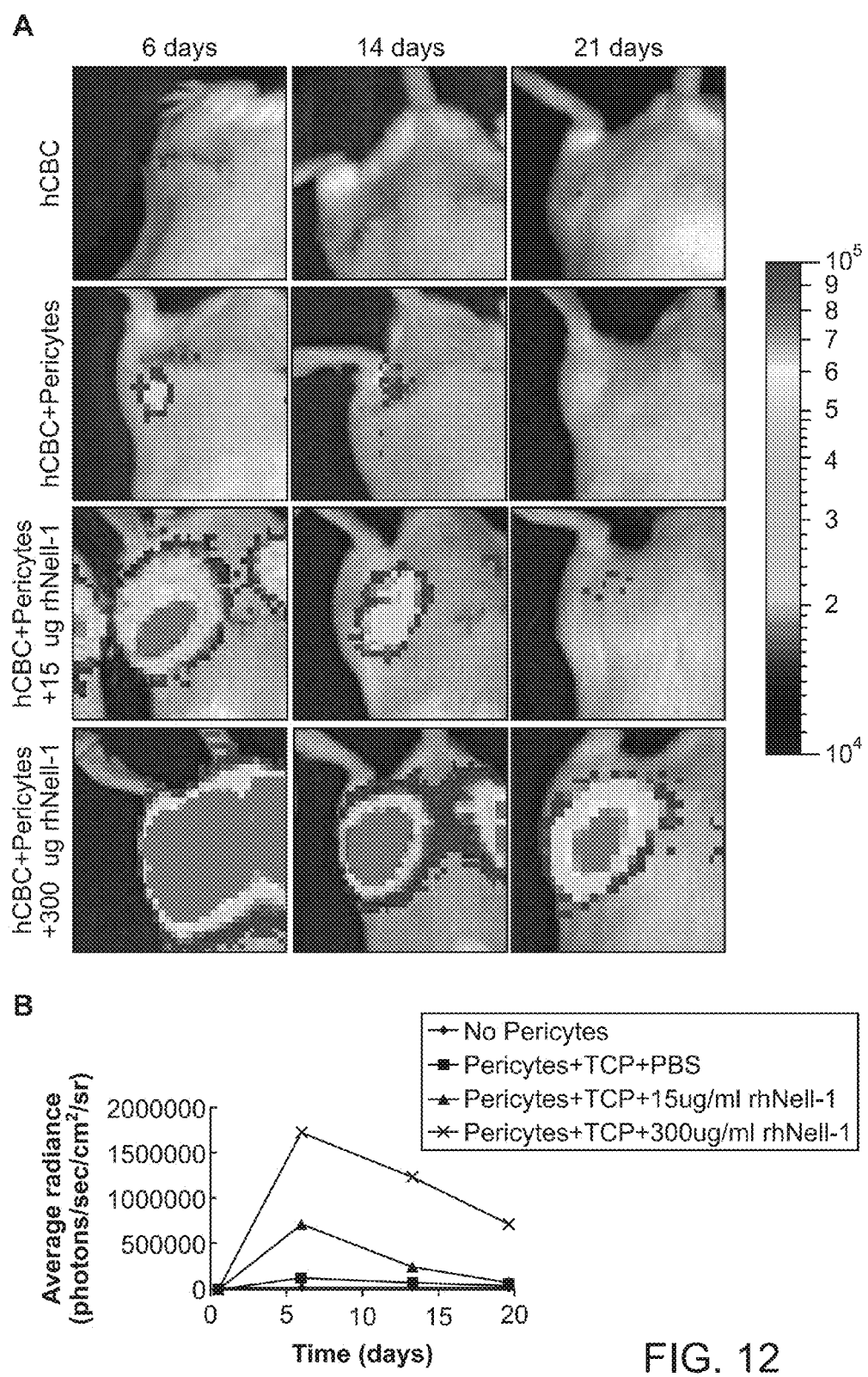
FIGS. 12A-12B show the results of experiments showing increased pericyte proliferation/survival when Nell-1 is added.
Figure 13:
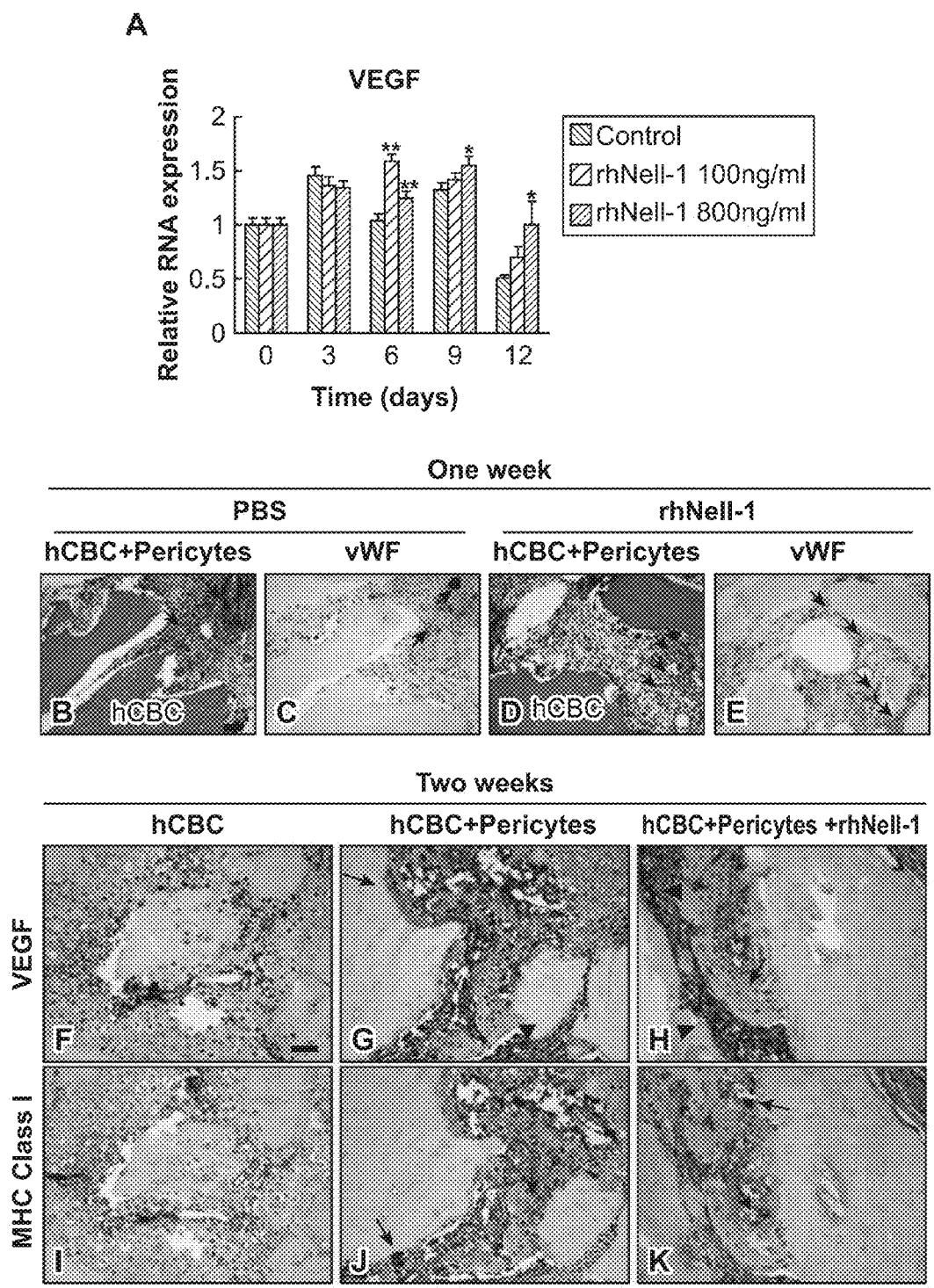
FIGS. 13A-13K show the results of experiments showing increased VEGF expression by pericytes when Nell-1 is added.

Experiments on osteogenic ability of pericytes and NELL-1 factor were performed in a SCID mouse thigh muscle implantation model. The results are shown in FIGS. 12 and 13. FIG. 12 shows increased pericyte proliferation/survival when Nell-1 is added. FIG. 13 shows increased VEGF expression by pericytes when Nell-1 is added.

The above results clearly documented the osteogenic ability of pericytes and NELL-1. These experiments demonstrate the effects of NELL-1 for enhancing survivability and engraftment of PSC or iPS and for causing PSC or iPS to differentiate into osteoblasts or progenitor cell lineage so as to generate a bone tissue.

While particular embodiments of the present invention have been shown and described, it are obvious to those skilled in the art that changes and modifications can be made without departing from this invention in its broader aspects. Therefore, the appended claims are to encompass within their scope all such changes and modifications as fall within the true spirit and scope of this invention.

We claim:

1. A method of treating or ameliorating a medical condition, comprising
    sorting a population of cells to obtain sorted perivascular stem cells identified by CD146, CD45, and CD34 antibodies as CD146−CD34+CD45− (adventitial cells) or CD146+CD34−CD45−(pericytes), and
    administering to a subject:
    the sorted adventitial cells or pericytes: or
    a composition comprising the sorted adventitial cells or pericytes;
    wherein the medical condition is associated with an injured or diseased tissue or organ, or wherein the medical condition is associated with a tissue or organ damaged by a disease or pathogen.

2. The method of claim 1, wherein the medical condition is associated with an injured or diseased tissue or organ.

3. The method of claim 1, wherein the medical condition is selected from the group consisting of a CNS (central nervous system) disease, a peripheral nervous system (PNS) disease, skin scarring, fibrosis, a tumor, cartilage injury, defect, or disease, a bone injury, defect, or disease, a cardiac condition, a kidney condition, a sport injury, a respiratory track disease, and diabetes.

4. The method of claim 1, wherein the medical condition is selected from the group consisting of Alzheimer's disease, Parkinson's disease, liver fibrosis, breast cancer, osteoporosis, heart attack, heart ischemia, renal ischemia, stroke, brain ischemia, injury to the spinal cord, meniscus tear, asthma, a lung disease, and type I diabetes.

5. The method of claim 1, wherein the tissue is selected from epithelial, connective, muscle, or nervous tissue, and wherein the organ is selected from the group consisting of skeletal, muscular, circulatory, nervous, respiratory, digestive, excretory, endocrine, reproductive, lymphatic and immune organs, skin, liver, stroma, meniscus, periodontal tissue, retina, cornea, eye, a facial organ, a limb, and any other body part.

* * * * *